US012703698B2

(12) United States Patent
Becker et al.

(10) Patent No.: US 12,703,698 B2
(45) Date of Patent: Aug. 11, 2026

(54) INHIBITORS OF INTERLEUKIN-1 RECEPTOR-ASSOCIATED KINASES 1 AND 4

(71) Applicant: The University of Rochester, Rochester, NY (US)

(72) Inventors: Michael Becker, Rochester, NY (US); Rakesh Singh, Rochester, NY (US); Richard Moore, Rochester, NY (US); Laura Calvi, Rochester, NY (US)

(73) Assignee: The University of Rochester, Rochester, NY (US)

( * ) Notice: Subject to any disclaimer, the term of this patent is extended or adjusted under 35 U.S.C. 154(b) by 726 days.

(21) Appl. No.: 18/017,759

(22) PCT Filed: Jul. 23, 2021

(86) PCT No.: PCT/US2021/042874
§ 371 (c)(1),
(2) Date: Jan. 24, 2023

(87) PCT Pub. No.: WO2022/020661
PCT Pub. Date: Jan. 27, 2022

(65) Prior Publication Data

US 2023/0295146 A1 Sep. 21, 2023

Related U.S. Application Data

(60) Provisional application No. 63/055,970, filed on Jul. 24, 2020.

(51) Int. Cl.
*C07D 417/02* (2006.01)
*A61K 45/06* (2006.01)
*A61P 35/00* (2006.01)

(52) U.S. Cl.
CPC ............ *C07D 417/02* (2013.01); *A61K 45/06* (2013.01); *A61P 35/00* (2018.01)

(58) Field of Classification Search
CPC .. C07D 417/02; C07D 417/14; C07D 413/02; C07D 413/14
See application file for complete search history.

(56) References Cited

U.S. PATENT DOCUMENTS 5,811,097 A 9/1998 Allison et al.
5,855,887 A 1/1999 Allison et al.
5,977,318 A 11/1999 Linsley et al.
6,051,227 A 4/2000 Allison et al.
6,207,156 B1 3/2001 Kuchroo et al.
6,682,736 B1 1/2004 Hanson et al.
6,984,720 B1 1/2006 Korman et al.
7,109,003 B2 9/2006 Hanson et al.
7,132,281 B2 11/2006 Hanson et al.
11,702,646 B2 7/2023 Bhattacharyya et al.
2002/0039581 A1 4/2002 Carreno et al.
2002/0086014 A1 7/2002 Korman et al.
2005/0201994 A1 9/2005 Korman et al.
2011/0257165 A1 10/2011 Pulici et al.
2013/0184287 A1 7/2013 Gray et al.
2016/0229856 A1 8/2016 Chen et al.
2019/0276426 A1 9/2019 Gray et al.
2020/0115383 A1 4/2020 Bryan et al.

FOREIGN PATENT DOCUMENTS

JP 2019-535789 A 12/2019
WO 98/42752 10/1998
WO 0037504 6/2000
WO 2001014424 3/2001
WO 2004035607 4/2004
WO 2011/043371 A1 4/2011
WO 2013/042137 A1 3/2013
WO 2018/098367 A1 5/2018
WO 2019/006126 A1 1/2019

OTHER PUBLICATIONS

Brown (Ed.), "Bioisosteres in Medicinal Chemistry", 2012, Wiley-VCH, 242 pgs. (Year: 2012).*
Buckley et al., "IRAK-4 inhibitors. Part 1: A series of amides", 2008, Bioorganic & Medicinal Chemistry Letters, 18, pp. 3211-3214 (Year: 2008).*
Wang et al., "IRAK-4 Inhibitors for Inflammation", 2009, Current Topics in Medicinal Chemistry, 9, pp. 724-737 (Year: 2009).*
Li, S. et al., IRAK-4: A novel member of the IRAK family with the properties of an IRAK-kinase. PNAS, 99 (2002), p. 5567.
Zhang, D. et al. Constitutive IRAK4 Activation Underlies Poor Prognosis and Chemoresistance in Pancreatic Ductal Adenocarcinoma. Clin. Canc. Res. (2016): doi: 10.1158/1078-0432.CCR-16-1121.
Li, Q. et al. IRAK4 mediates colitis-induced tumorigenesis and chemoresistance in colorectal cancer. JCI Insight 4(19), (2019), e130867.
*Remington's Pharmaceutical Sciences*, 17th ed., Mack Publishing Company, Easton, PA., p. 1418 (1985).
Hurwitz et al., CTLA-4 blockade synergizes with tumor-derived granulocyte-macrophage colony-stimulating factor for treatment of an experimental mammary carcinoma. Proc. Natl. Acad. Sci. USA, 95(17):10067-10071 (1998).
Camacho et al., Phase 1 clinical trial of anti-CTLA4 human monoclonal antibody CP-675,206 in patients (pts) with advanced solid malignancies. J. Clin. Oncology, 22(145): Abstract No. 2505 (2004) (antibody CP-675206).
Mokyr et al., Realization of the Therapeutic Potential of CTLA-4 Blockade in Low-Dose Chemotherapy-treated Tumor-bearing Micel. Cancer Res., 58:5301-5304 (1998).

(Continued)

*Primary Examiner* — Brenda L Coleman
*Assistant Examiner* — Madeline E Braun
(74) *Attorney, Agent, or Firm* — Meunier Carlin & Curfman LLC

(57) ABSTRACT

The present disclosure provides compounds that are inhibitors of interleukin-1 receptor-associated kinases 1 and 4 (IRAK1 and IRAK4) and their use in the treatment of medical disorders such as autoimmune disorders, cancer, and pain disorders.

3 Claims, 14 Drawing Sheets

(56) References Cited

OTHER PUBLICATIONS

A. Mullard, "New checkpoint inhibitors ride the immunotherapy tsunami," Nature Reviews: Drug Discovery (2013), 12:489- 492.

Second Office Action received in corresponding Chinese Application No. 202180054152.8, dated Mar. 18, 2025.

Office Action received in corresponding Japanese Application No. 2023-504544, dated Apr. 22, 2025.

International Search Report and Written Opinion received in PCT/US2021/042874, mailed Oct. 7, 2023, 11 pages.

Search Report received in Chinese Application No. 2021800541528, mailed Sep. 14, 2024.

Office Action received in Chinese Application No. 2021800541528, mailed Sep. 14, 2024.

* cited by examiner

UR241-2

Cluster 1 Size: 183, En: -50.4 kcal/mol

Cluster 1 Size: 1, En: -51.7 kcal/mol

UR241-1

THP-1 NF-kB reporter assay

PF06650833

THP-1 NF-kB reporter assay

UR241-2 B1

THP-1 NF-kB reporter assay

UR241-2 B3

THP-1 NF-kB reporter assay

UR241-1

MDSL NF-kB reporter assay

PF06650833

MDSL NF-kB reporter assay

UR241-2 B3

UR241-1

PANC-1 NF-kB reporter asssay

INHIBITORS OF INTERLEUKIN-1 RECEPTOR-ASSOCIATED KINASES 1 AND 4

CROSS-REFERENCE TO RELATED APPLICATIONS

This application is a U.S. National Stage application filed under 35 U.S.C. § 371 of PCT/US2021/042874 filed Jul. 23, 2021, which claims the benefit of priority to U.S. Provisional Application No. 63/055,970 filed Jul. 24, 2020, the disclosure of which is hereby incorporated herein by reference in its entirety.

TECHNICAL FIELD

This disclosure relates to compounds for the treatment of medical disorders, and more particularly to compounds that are inhibitors of interleukin-1 receptor-associated kinases 1 and 4 (IRAK1 and IRAK4) and uses thereof.

BACKGROUND

Interleukin receptor-associated kinase 4 (IRAK4) is a key functional member of the IRAK family of intracellular serine-threonine kinases consisting of IRAK1, IRAK2, IRAK3, and IRAK4 (see S. Li et al. PNAS, 99 (2002), p. 5567). IRAK4 is a downstream signaling mediator of the pro-inflammatory IL-1 family of receptors and of the pathogen sensing and innate signaling toll-like receptors (TLRs). The TLRs are activated by endogenous pathogens associated with necrotic cell death and tissue damage, the critical hallmarks of chronic inflammatory processes. Aberrant expression of IRAK4 orchestrates chronic inflammatory diseases, such as rheumatoid arthritis and lupus. Aberrant signaling of the IRAK4 pathway due to activating mutations in the MyD88 adaptor protein has also be implicated in malignancies. The proximal location of IRAK4 to immune signaling receptors (TLRs and IL-1R) has generated significant interest in therapeutic targeting of IRAK4 for mounting control against autoimmune and inflammatory diseases. Therapeutic agents targeting IRAK4 are also suggested to be useful in controlling high-risk malignancies such as pancreatic cancer (see D. Zhang et al. Clin. Canc. Res. (2016): doi: 10.1158/1078-0432.CCR-16-1121), colitis-induced tumorigenesis and chemoresistance in colorectal cancer (Q. Li et al. JCI Insight 4(19), (2019), e130867).

According to the National Institutes of Health, up to 23.5 million Americans (>7% of the population) suffer from one or another form of disease classified as autoimmune disease—and the prevalence is rising (see NIH Autoimmune Diseases Coordinating Committee: Autoimmune Diseases Research Plan, March 2005). In one aspect, the autoimmune disease can lead the body to produce antibodies that instead of fighting infections, will attach the body's cells, tissues and organs. Autoimmune diseases may occur almost anywhere in the body, and some may affect more than one part of the body. Autoimmune diseases are also characterized by inadequate and severe unmet medical needs. Similarly, more than 1.5 million new cancer cases were diagnosed in 2012, many of which are orchestrated by aberrant IRAK4 signaling directly or indirectly. There is a clear need to develop new therapies targeting the IRAK family, particularly IRAK1 and IRAK4, for treatment of immune disorder and malignancies.

SUMMARY

The present disclosure provides compounds that are inhibitors of interleukin receptor-associated kinases 1 and 4 (IRAK1 and IRAK4), along with methods for treating disorders associated with aberrant expression or signaling of IRAK1 and/or IRAK4 using the compounds described herein.

Thus, in one aspect, a compound of Formula I is provided:

(I)

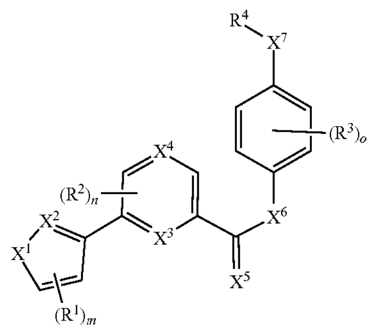

or a pharmaceutically acceptable salt, solvate, or prodrug thereof;

wherein all variables are further defined herein.

Pharmaceutical compositions are also provided comprising a compound as described herein, or a pharmaceutically acceptable salt, solvate, or prodrug thereof, and a pharmaceutically acceptable carrier.

In another aspect, a method of treating a medical disorder in a subject associated with aberrant expression or signaling of IRAK1 and/or IRAK4 comprising administering to the subject a therapeutically effective amount of a compound described herein, or a pharmaceutically acceptable salt, solvate, or prodrug thereof.

In some embodiments, the medical disorder comprises a cancer. In some embodiments, the medical disorder comprises an autoimmune disorder. In another aspect, the medical disorder comprises a pain disorder, for example neuropathic pain or nociceptive pain.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

μM. FIG. 2A: UR241-1. FIG. 2B: PF06650833. FIGs. C and D: UR241-2 Batch 1 and 3 (B1, B3). Cells were pre-treated with drugs for 30 min and treated with hIL-1f3 for another 6 hr.

(FIG. 6A) UR241-1 and (FIG. 6B) UR241-2 suppressed the colonies formed by MDS-L cells dose dependently.

Like reference symbols in the various drawings indicate like elements.

DETAILED DESCRIPTION

Figure 1A:
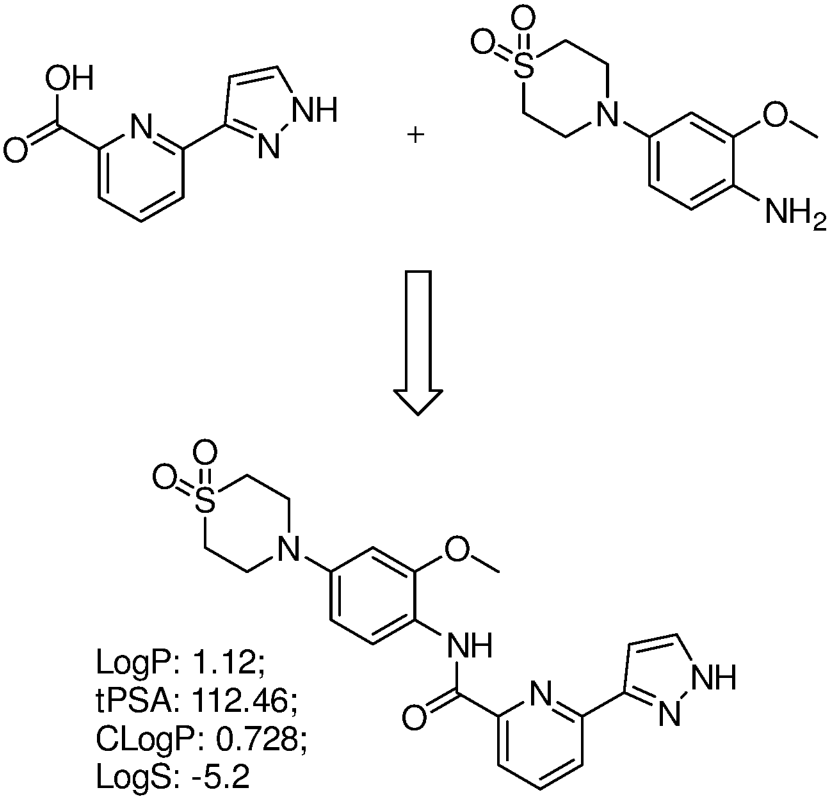
FIG. 1A shows the synthetic scheme and chemical structure of UR241-1.
Figure 1B:
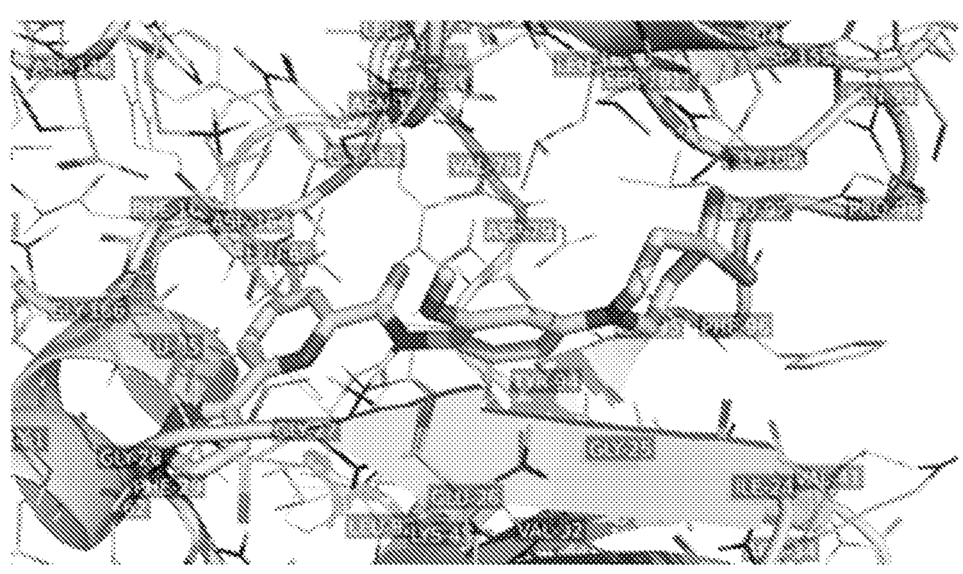
FIG. 1B shows the in silico predicted interaction of UR241-2 with IRAK-1.
Figure 1C:
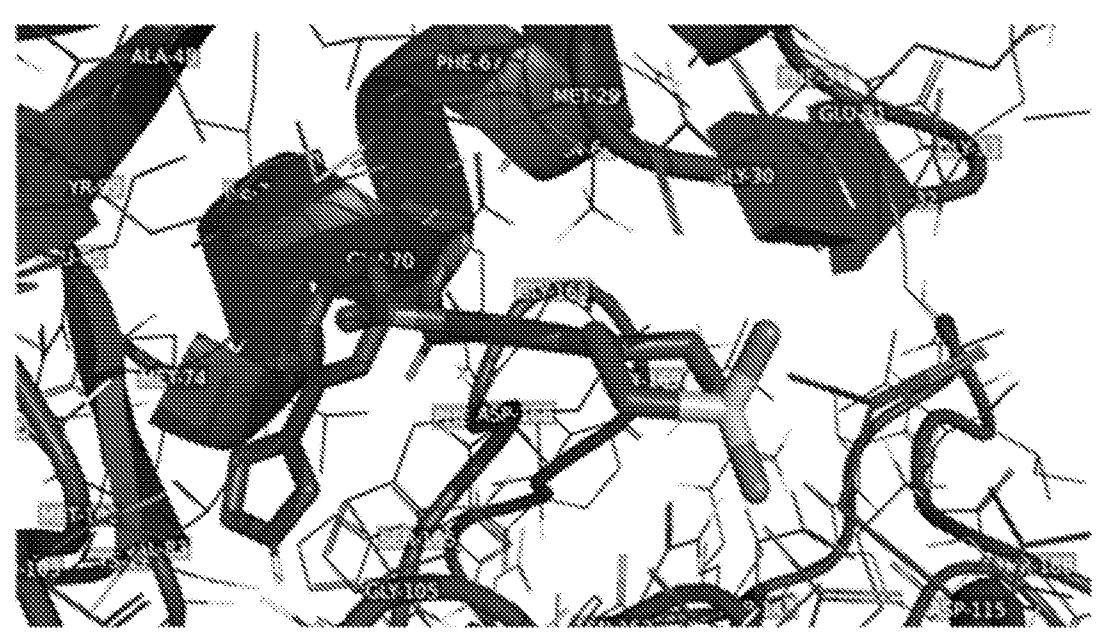
FIG. 1C shows the in silico predicted interaction of UR241-2 with IRAK-4.
Figure 1D:
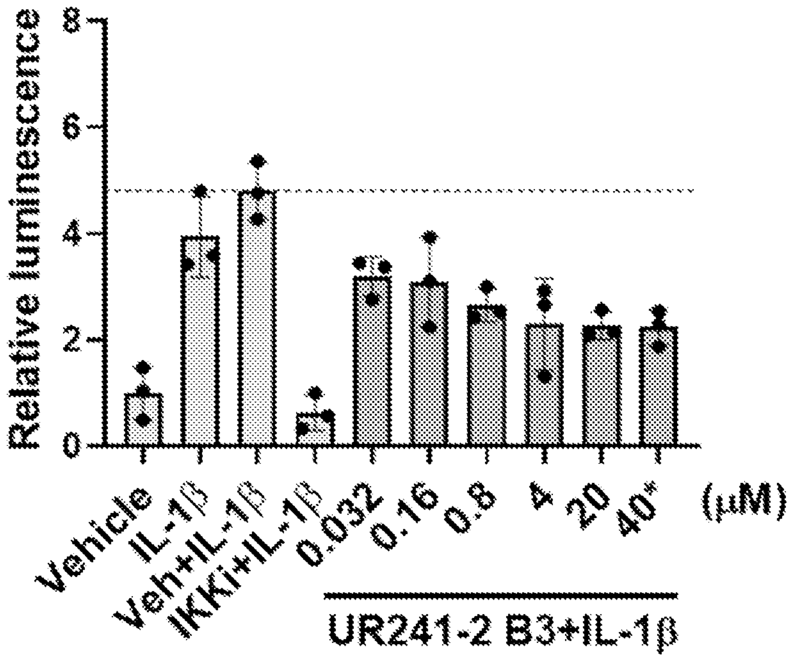
FIG. 1D shows that UR241-2 dose-dependently inhibited IL1b inducted NF-kB activity in a human leukemia THP-1 reporter cell line.
Figure 1E:
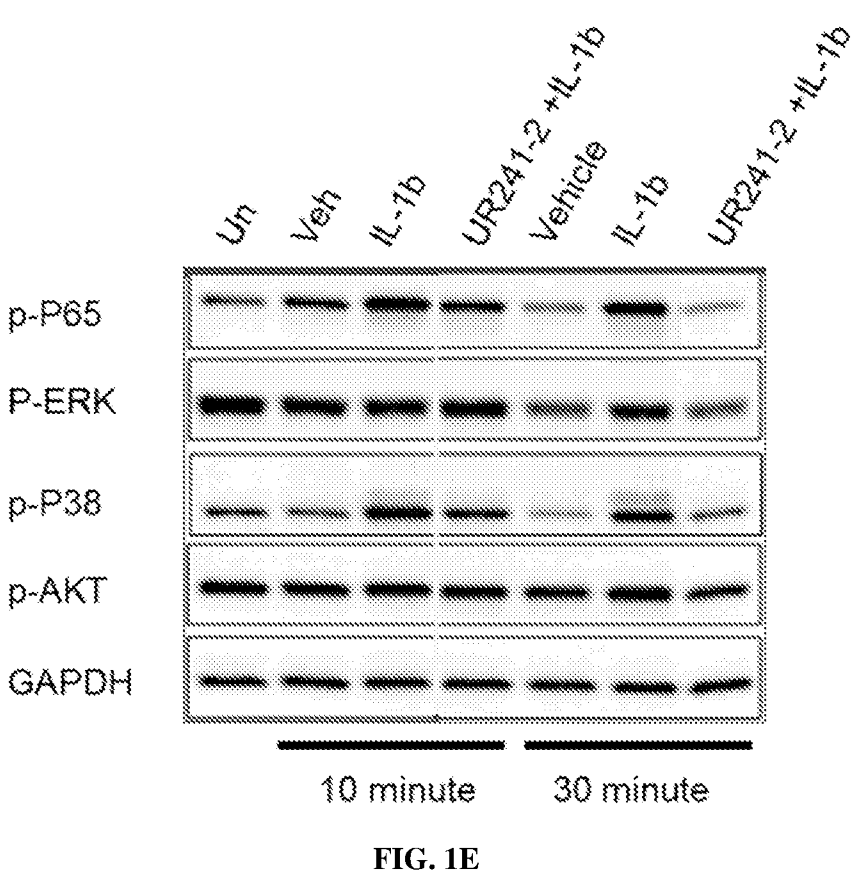
FIG. 1E shows UR241-2 inhibition IL1b signaling events in THP-1 cells at 10 and 30 minutes [hIL-1β 10 ng/mL, UR241-2 4 μM, WB 30 μg/lane].
Figure 1F:
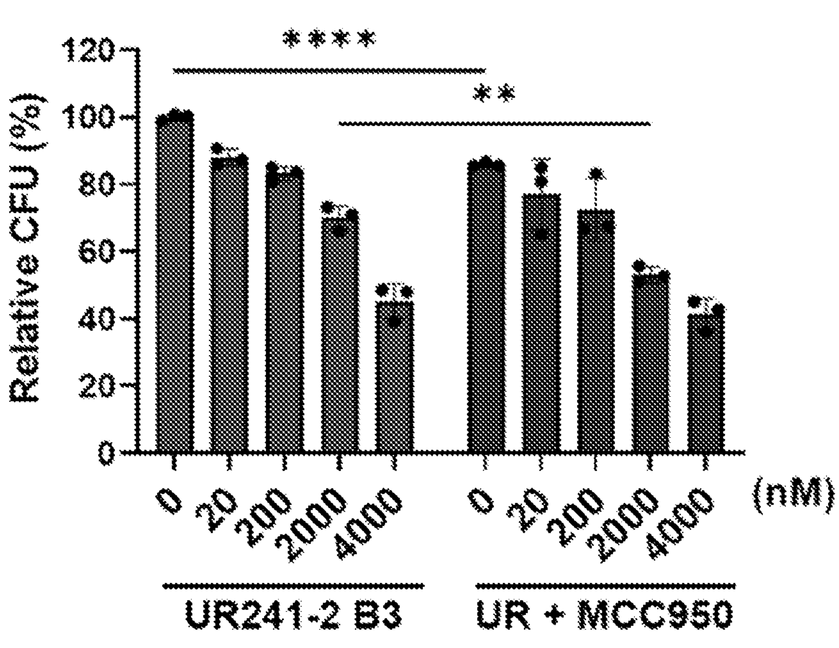
FIG. 1F shows UR241-2 (4 uM) with and without MCC950 (100 nM) inhibition of colony forming activity in methylcellulose culture in murine MLL-AF9 leukemia.
Figure 2A:
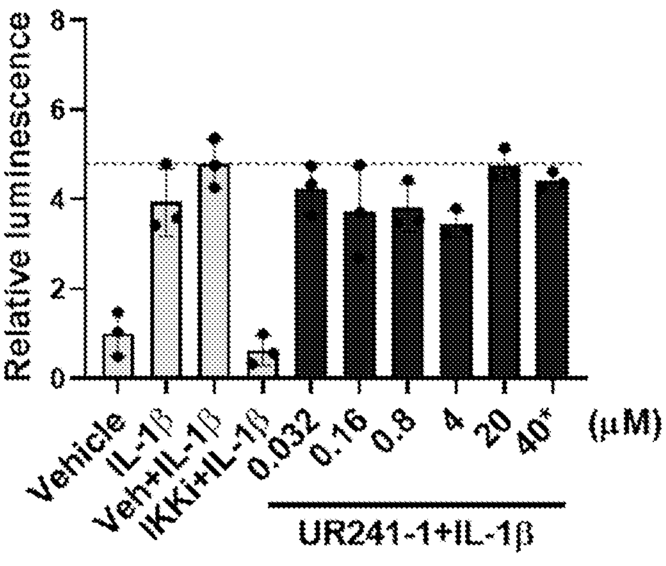
FIGS. 2A, 2B, 2C, and 2D show the effect of IRAK-1 and -4 inhibitor in a THP-1 NF-kB assay. THP-1 (1e4 cells/0.1 mL/well) seeded in a 96 well white plate were treated with vehicle (DMS) 0.4%, hIL-1β 10 ng/mL, IKK2 inhibitor 20
Figure 2B:
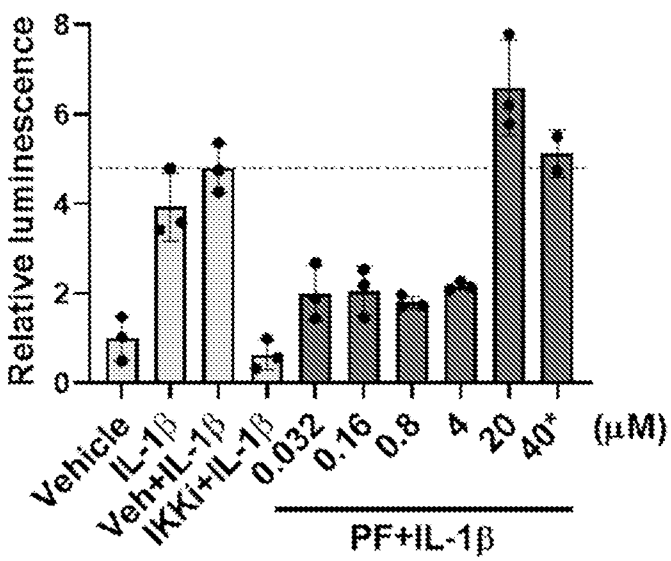
Figure 2C:
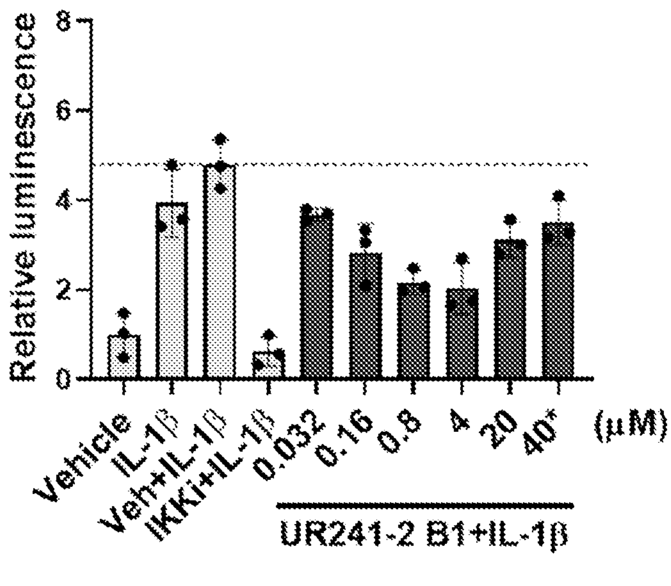
Figure 2D:
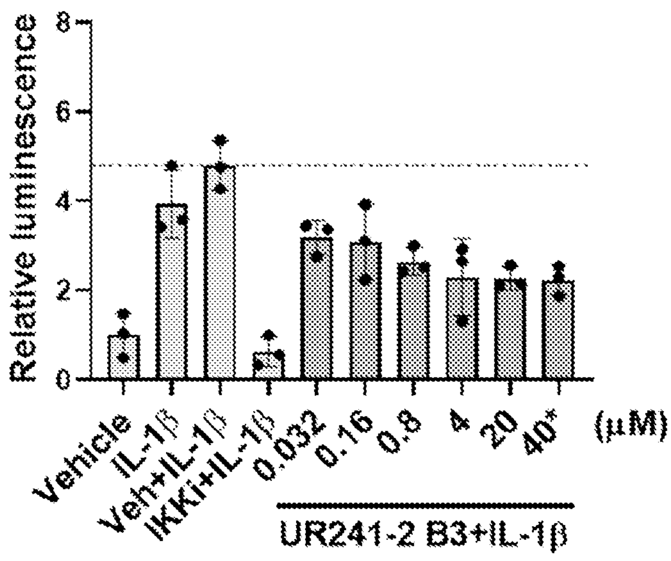
Figure 3:
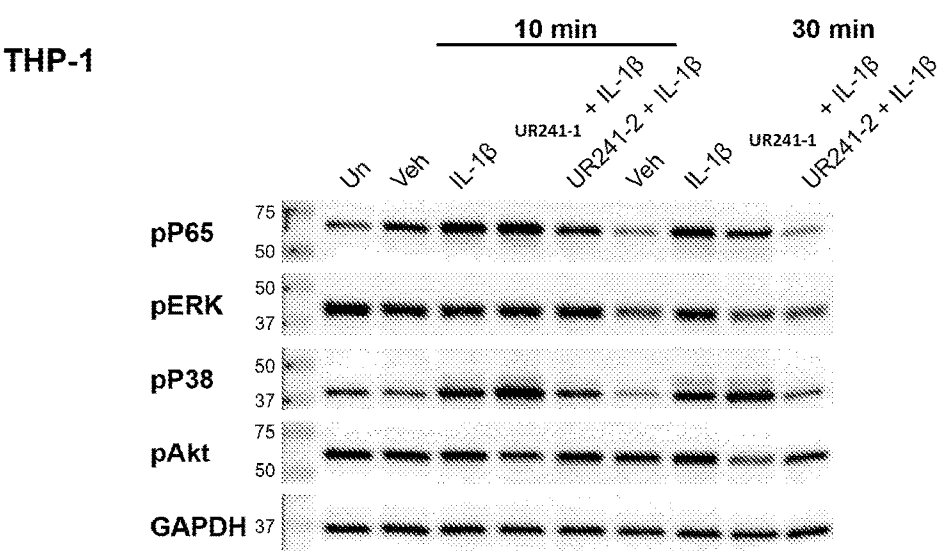
FIG. 3 shows the effect of UR241-1 and UR241-2, the representative compounds of those disclosed herein, on the expression of MAPkinases expression in THP-1 cells. Whole cell lysates of THP1 treated with vehicle, hIL-1B (10 ng/mL), UR241-1 (10 μM) and UR241-2 (4 μM) for 10 minutes and 30 minutes. 30 μg proteins were electrophoresed and probed with phospho-/native p65, phospho-p38, pAKT, and GAPDH.
Figure 4A:
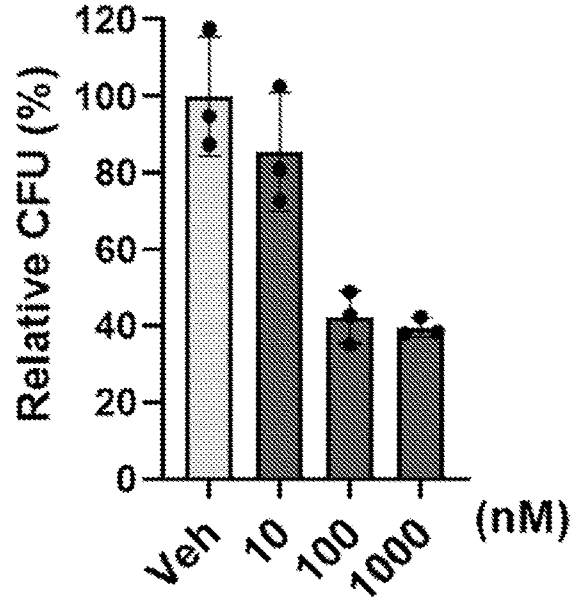
FIGS. 4A, 4B and 4C show the effect of MCC950 (reference), UR241-1, and UR241-2 on the colony formation potential of THP-1 cells in vitro. MCC-950 (FIG. 4A0, UR241-1 (FIG. 4B), and UR241-2 (FIG. 4C) suppressed the colonies formed by THP-1 cells dose-dependently.
Figure 4B:
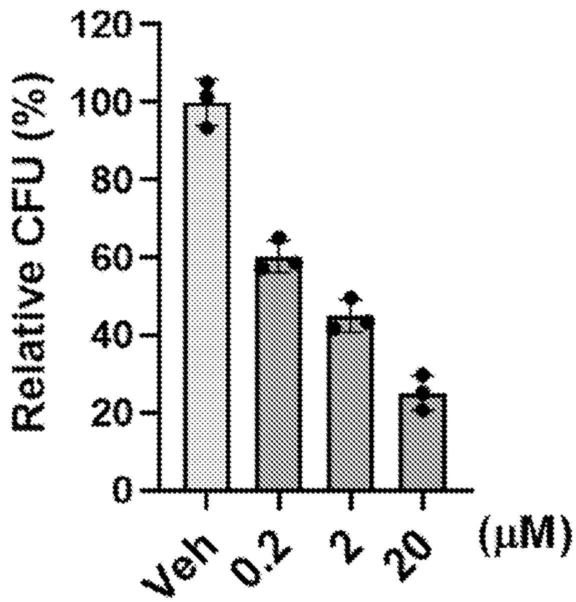
Figure 4C:
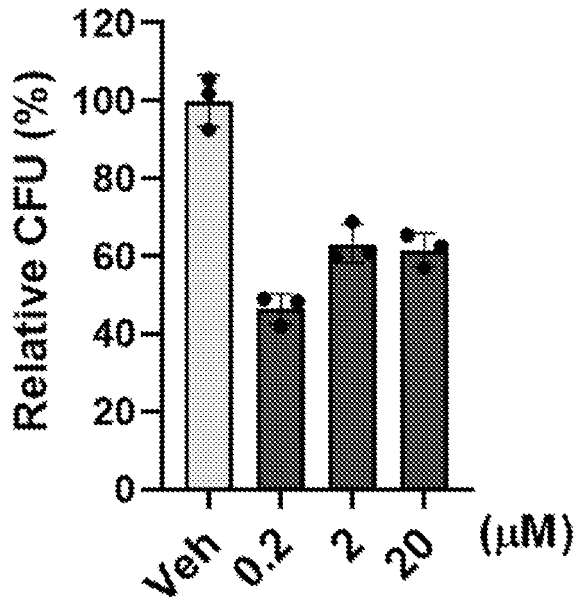
Figure 5A:
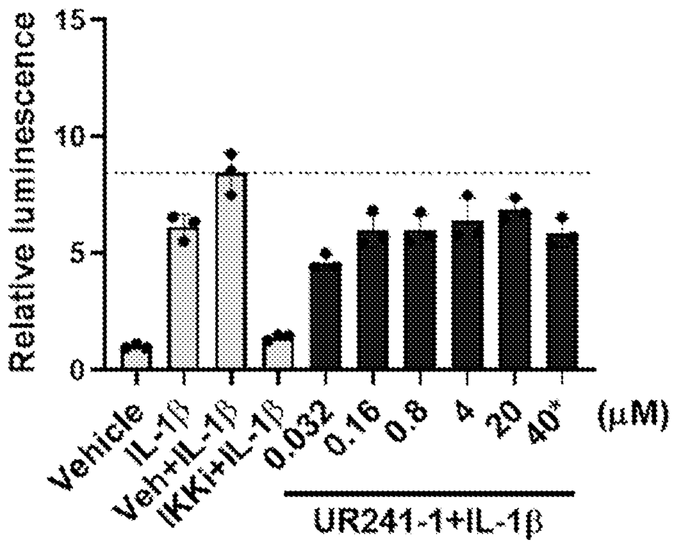
FIGS. 5A, 5B, 5C, and 5D show the relative inhibition of NF-kB reporter activity in stably transfected THP-1 cells upon treatment with UR241-1 (FIG. 5A), PF06650833 (FIG. 5B), UR241-2, batch 1 (FIG. 5C), and UR241-2, batch 3 (FIG. 5D).
Figure 5B:
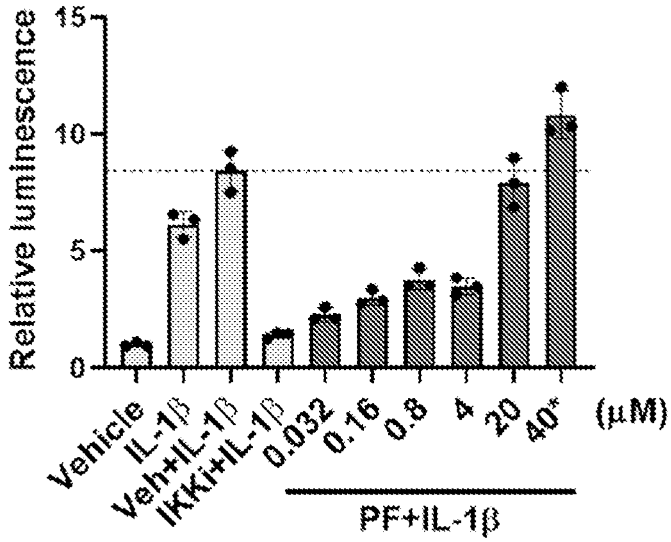
Figure 5C:
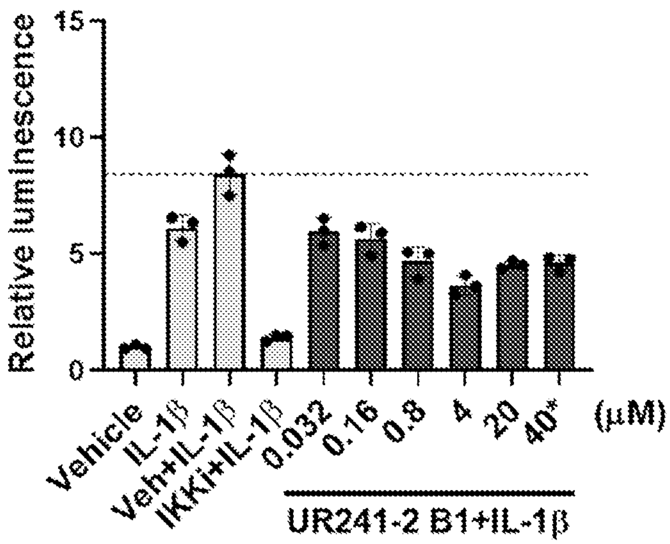
Figure 5D:
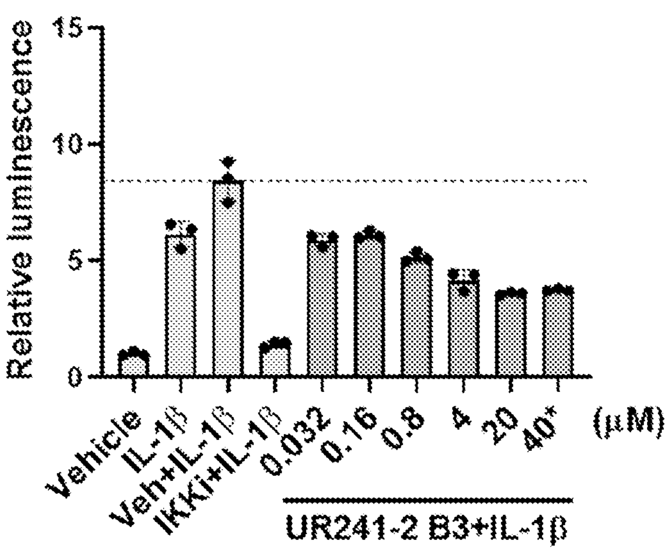
Figure 6A:
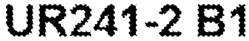
FIGS. 6A and 6B show the effect of UR241-1 and UR241-2 on the colony formation potential of MDS-L cells in vitro.
Figure 6A:
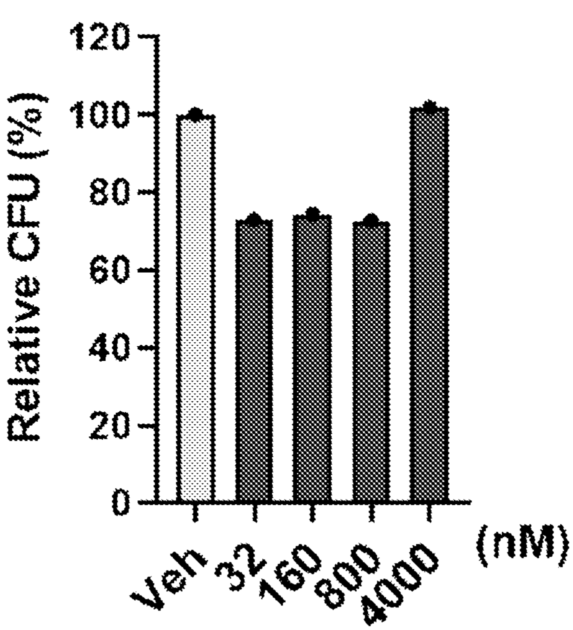
Figure 6B:
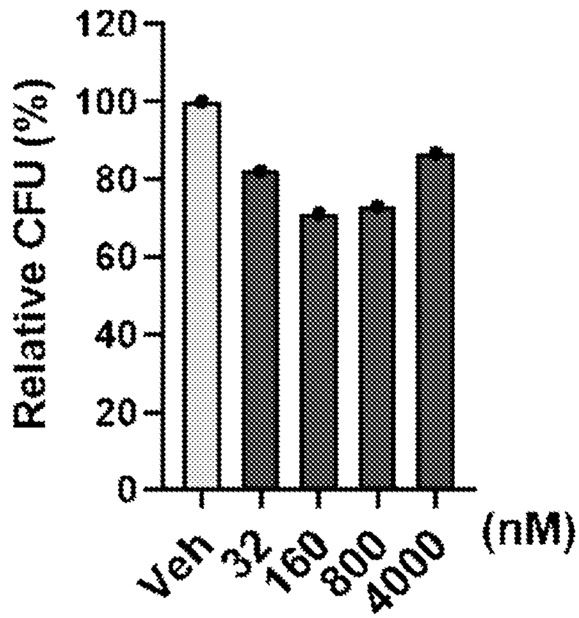
Figure 7A:
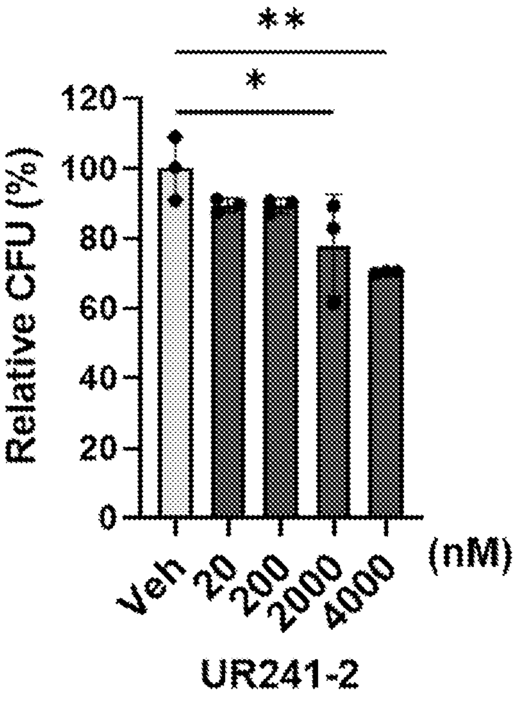
FIGS. 7A, 7B and 7C show UR241-2 (FIG. 7A), PF-06650833 (FIG. 7B, reference), and MCC950 (FIG. 7C, reference) treatment inhibited colony formation of MDS-L cells in vitro, dose-dependently.
Figure 7B:
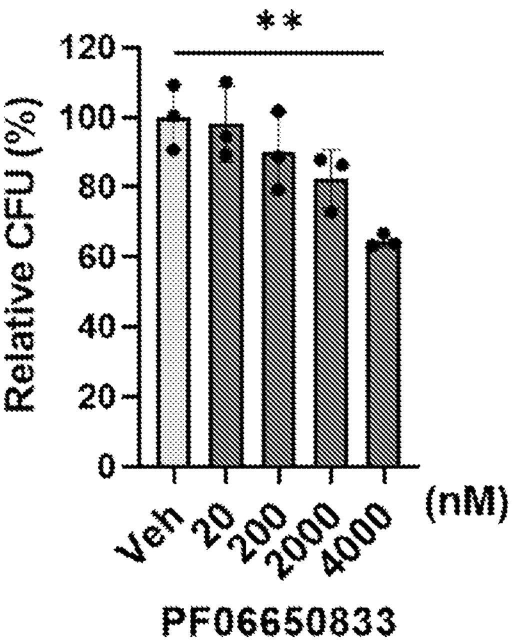
Figure 7C:
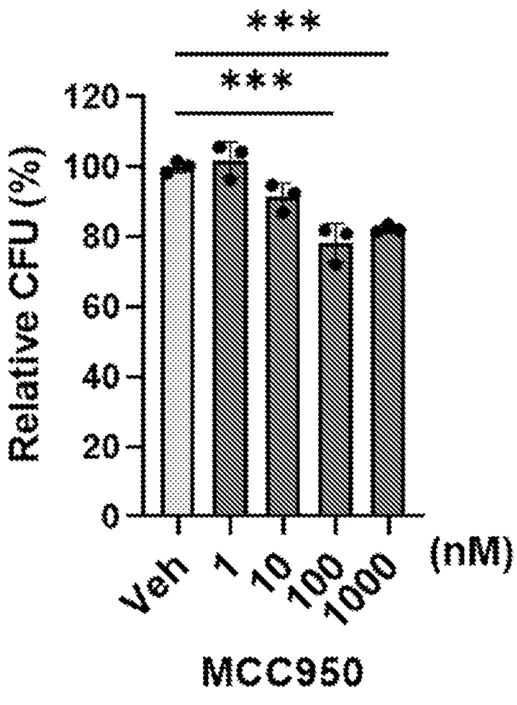
Figure 8A:
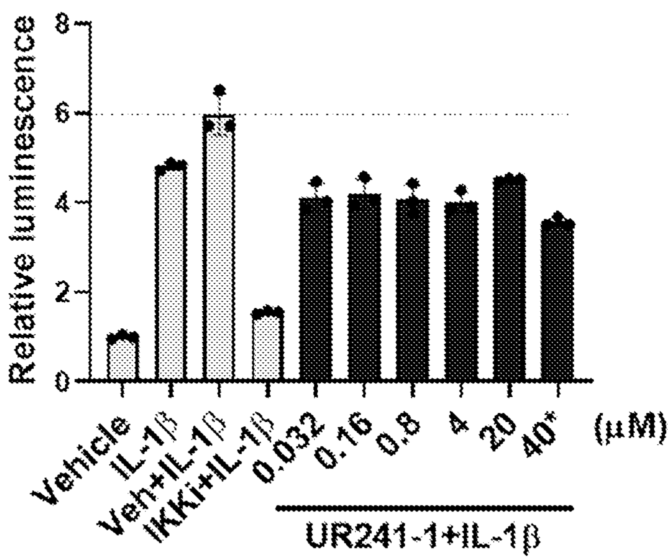
FIGS. 8A, 8B, 8C, and 8D show inhibition of NF-kB reporter activity in PANC-1 pancreatic cancer cells by UR241-1 (FIG. 8A), UR241-2 batch 1 (FIG. 8B), UR241-2 batch 2 (FIG. 8C), and UR241-2 batch 3 (FIG. 8D).
Figure 8B:
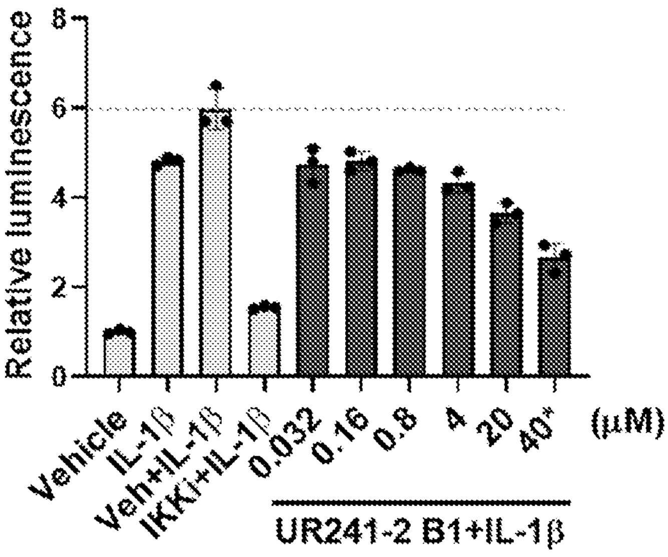
Figure 8C:
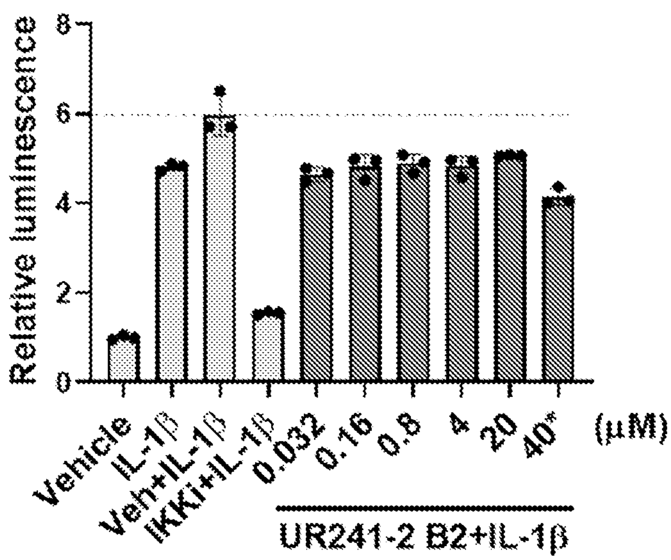
Figure 8D:
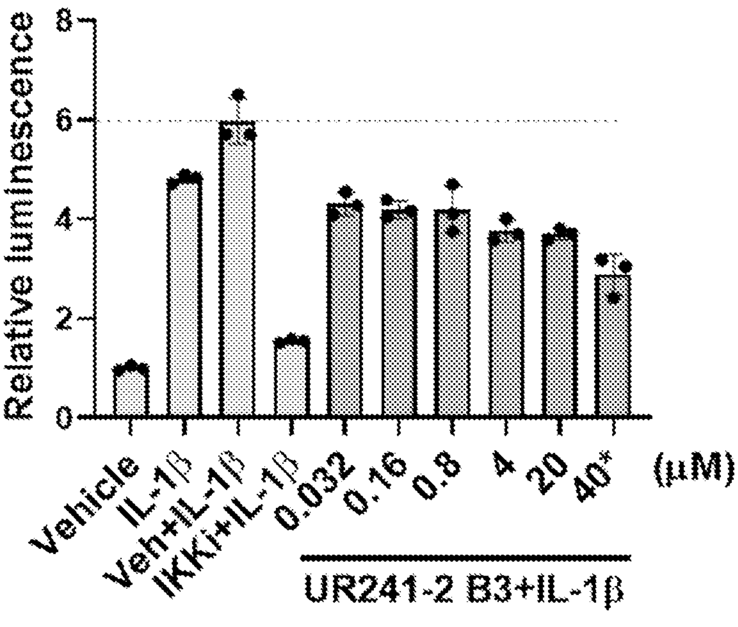

Many modifications and other embodiments disclosed herein will come to mind to one skilled in the art to which the disclosed compounds, compositions and methods pertain having the benefit of the teaching presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of the disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from and combined with the features of any of the other several embodiments without departing from the scope and spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuations, or the number or type of aspects described in the specification.

All publications mentioned herein are incorporated herein by reference to disclose and described the methods and/or materials in connection with which the publications are cited. The publications discussed herein are provided solely for the disclosure prior to the filing date of the present application. The dates of publication provided herein can be different from the actual publication dates, which can require independent confirmation.

It is also to be understood that the terminology used herein is for the purpose of describing particular aspects only and is not intended to be limited. Unless defined otherwise, all technical and scientific terms used herein have the same meaning as commonly understood by one of ordinary skill in the art to which the disclosed compounds, compositions, and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, “comprising” is to be interpreted as specifying the presence of the stated feature, integers, steps, or components as referred to, but does not preclude the presence or addition of one or more features, integers, steps, or components, or groups thereof. Moreover, each of the terms “by”, “comprising”, “comprises”, “comprised of”, “including”, “includes”, “included”, “involving”, “involves”, “involved”, and “such as” are used in their open, non-limiting sense and may be used interchangeably. Further, the term “comprising” is intended to include examples and aspects encompassed by the terms “consisting essentially of” and “consisting of”. Similarly, the term “consisting essentially of” is intended to include examples encompassed by the term “consisting of”.

As used in the specification and the appended claims, the singular forms “a”, “an” and “the” include plural referents unless the context clearly dictates otherwise. Thus, for example, reference to “a compound”, “a pharmaceutical compositions”, or “a medical disorder” includes, but is not limited to, two or more such compounds, pharmaceutical compositions, or medical disorders, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that value is also herein disclosed as “about” that particular value in addition to the value itself. For example, if the value “10” is disclosed, then “about 10” is also disclosed. Ranges can be expressed herein as from "about" one particular value, and/or to "about" another particular value. Similarly, when values are expressed as approximations, by use of the antecedent "about", it will be understood that the particular value forms a further aspect. For example, if the value "about 10" is disclosed, then "10" is also disclosed.

As used herein, the terms "about", "approximate", "at or about", and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably be determined. In such cases, it is generally understood, as used herein, that "about" and "at or about" mean the nominal value indicated ±10% variation unless otherwise indicated or inferred. In general, an amount, size, formulation, parameter, or other quantity or characteristic is "about", "approximate", or "at or about" whether or not expressly stated to be such. It is understood that where "about", "approximate", or "at or about" is used before a quantitative value, the parameter also includes the specific quantitative value itself, unless specifically stated otherwise.

As used herein "effective amount" can refer to the amount of a disclosed compound or pharmaceutical composition provided herein that is sufficient to effect beneficial or desired biological, emotional, medicinal, or clinical response of a cell, tissue, system, animal, or human. An effective amount can be administered in one or more administrations, applications, or dosages. The term can also include within its scope amounts effective to enhance or restore substantially normal physiological function.

As used herein, the term "therapeutically effective amount" refers to an amount that is sufficient to achieve the desired therapeutic result or to have an effect an undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desired to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgement. It will be understood by those of ordinary skill in the art, however, that a patient may insist upon a lower dose or tolerable dose for medical reasons, psychological reasons or for virtually any other reasons.

A response to a therapeutically effective dose of a disclosed compound or pharmaceutical composition can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary and can be administered in one or more dose administrations daily for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "optional" or "optionally" means that the subsequently described event or circumstance can or cannot occur, and that the description includes instances where said event or circumstance occurs and instances where it does not.

As used interchangeably herein, "subject", "individual", or "patient" can refer to a vertebrate organism, such as a mammal (e.g., human). "Subject" can also refer to a cell, a population of cells, a tissue, an organ, or an organism, preferably to a human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a medical disorder. The effect can be therapeutic in terms of a partial or complete cure of a disease, condition, symptom or adverse effect attributed to the disease, disorder or condition. The term "treatment" as used herein can include any treatment of a medical disorder in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (i.e., subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose", "unit dose", or "dosage" can refer to physically discrete units suitable for use in a subject, each unit containing predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing the rate of advancement of a disease, disorder, condition, or side effect.

Chemical Definitions

Compounds are described using standard nomenclature. Unless defined otherwise, all technical and scientific terms used herein have the same meaning as is commonly understood by one of skill in the art to which this invention belongs.

The compounds described herein include enantiomers, mixtures of enantiomers, diastereomers, tautomers, racemates and other isomers, such as rotamers, as if each is specifically described, unless otherwise indicated or otherwise excluded by context.

A dash ("-") that is not between two letters or symbols is used to indicate a point of attachment for a substituent. For example, $-(C{=}O)NH_2$ is attached through the carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example, a pyridyl group substituted by oxo is a pyridine. Combinations of substituents and/or variables are permissible only if such combinations result in stable compounds or useful synthetic intermediates. A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Non-limiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to: alkyl, haloalkyl, alkoxy, alkenyl, alkynyl, aryl, heteroaryl, cycloalkyl, heterocycle, aldehyde, amino, carboxylic acid, ester, ether, halo, hydroxy, keto, nitro, cyano, azido, silyl, sulfo-oxo, sulfonyl, sulfone, sulfoxide, sulfonylamino, or thiol.

"Alkyl" is a straight chain or branched saturated aliphatic hydrocarbon group. In certain embodiments, the alkyl is $C_1$-$C_2$, $C_1$-$C_3$, or $C_1$-$C_6$ (i.e., the alkyl chain can be 1, 2, 3, 4, 5, or 6 carbons in length). The specified ranges as used herein indicate an alkyl group with length of each member of the range described as an independent species. For example, $C_1$-$C_6$alkyl as used herein indicates an alkyl group having from 1, 2, 3, 4, 5, or 6 carbon atoms and is intended to mean that each of these is described as an independent species and $C_1$-$C_4$alkyl as used herein indicates an alkyl group having from 1, 2, 3, or 4 carbon atoms and is intended to mean that each of these is described as an independent species. When $C_0$-$C_n$alkyl is used herein in conjunction with another group, for example ($C_3$-$C_7$ cycloalkyl)$C_0$-$C_4$alkyl, or $-C_0$-$C_4$($C_3$-$C_7$cycloalkyl), the indicated group, in this case cycloalkyl, is either directly bound by a single covalent bond ($C_0$alkyl), or attached by an alkyl chain, in this case 1, 2, 3, or 4 carbon atoms. Alkyls can also be attached via other groups such as heteroatoms, as in $-O-C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In one embodiments, the alkyl group is optionally substituted as described herein.

"Cycloalkyl" is a saturated mono- or multi-cyclic hydrocarbon ring system. When composed of two or more rings, the rings may be joined together in a fused or bridged fashion. Non-limiting examples of typical cycloalkyl groups include cyclopropyl, cyclobutyl, cyclopentyl, cyclohexyl, and cycloheptyl. In one embodiment, the cycloalkyl group is optionally substituted as described herein.

"Alkenyl" is a straight or branched chain aliphatic hydrocarbon group having one or more carbon-carbon double bonds, each of which is independently either cis or trans, that may occur at a stable point along the chain. Non-limiting examples include $C_2$-$C_4$alkenyl and $C_2$-$C_6$alkenyl (i.e., having 2, 3, 4, 5, or 6 carbons). The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described herein.

"Alknyl" is a straight or branched chain aliphatic hydrocarbon group having one or more carbon-carbon triple bonds that may occur at any stable point along the chain, for example, $C_2$-$C_4$alkynyl or $C_2$-$C_6$alkynyl (i.e., having 2, 3, 4, 5, or 6 carbons). The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl. In one embodiment, the alkynyl group is optionally substituted as described herein.

"Alkoxy" is an alkyl group as defined above covalently bound through an oxygen bridge (—O—). Examples of alkoxy include, but are not limited to, methoxy, ethoy, n-propoxy, isopropoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, and 3-methylpentoxy. Similarly, an "alkylthio" or "thioalkyl" group is an alkyl group as defined above with the indicated number of carbon atoms covalently bound through a sulfur bridge (—S—). In one embodiment, the alkoxy group is optionally substituted as described herein.

"Alkanoyl" is an alkyl group as defined above covalently bound through a carbonyl (C═O) bridge. The carbonyl carbon is included in the number of carbons, for example $C_2$alkanoyl is a $CH_3$(C═O)— group. In one embodiment, the alkanoyl group is optionally substituted as described herein.

"Haloalkoxy" indicates a haloalkyl group as defined herein attached through an oxygen bridge (oxygen of an alcohol radical).

"Halo" or "halogen" indicates, independently, any of fluoro, chloro, bromo or iodo.

"Aryl" indicates an aromatic group containing only carbon in the aromatic ring or rings. In one embodiment, the aryl group contains 1 to 3 separate or fused rings and is 6 to 14 or 18 ring atoms, without heteroatoms as ring members. When indicated, such aryl groups may be further substituted with carbon or non-carbon atoms or groups. Such substitution may include fusion to a 4- to 7- or 5- to 7-membered saturated or partially unsaturated cyclic group that optionally contains 1, 2, or 3 heteroatoms independently selected from N, O, B, P, Si and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described herein.

The term "heterocycle" refers to saturated and partially saturated heteroatom-containing ring radicals, where the heteroatoms may be selected from N, O, and S. The term heterocycle includes monocyclic 3-12 members rings, as well as bicyclic 5-16 membered ring systems (which can include fused, bridged, or spiro bicyclic ring systems). It does not include rings containing —O—O—, —O—S—, and —S—S— portions. Examples of saturated heterocycle groups including saturated 4- to 7-membered monocyclic groups containing 1 to 4 nitrogen atoms [e.g., pyrrolidinyl, imidazolidinyl, piperidinyl, pyrrolinyl, azetidinyl, piperazinyl, and pyrazolidinyl]; saturated 4- to 6-membered monocyclic groups containing 1 to 2 oxygen atoms and 1 to 3 nitrogen atoms [e.g., morpholinyl]; and saturated 3- to 6-membered heteromonocyclic groups containing 1 to 2 sulfur atoms and 1 to 3 nitrogen atoms [e.g., thiazolidinyl]. Examples of partially saturated heterocycle radicals include, but are not limited, dihydrothienyl, dihydropyranyl, dihydrofuryl, and dihydrothiazolyl. Examples of partially saturated and saturated heterocycle groups include, but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydroquinolyl, 2,3,4,4a,9,9a-hexahydro-1H-3-aza-fluorenyl, 5,6,7-trihydro-1,2,4-triazolo [3,4-a]isoquinolyl, 3,4-dihydro-2H-benzo[1,4]oxazinyl, benzo[1,4]dioxanyl, 2,3,-dihydro-1H-benzo[d]isothazol-6-yl, dihydropyranyl, dihydrofuryl, and dihydrothiazolyl. Bicyclic heterocycle includes groups wherein the heterocyclic radical is fused with an aryl radical wherein the point of attachment is the heterocycle ring. Bicyclic heterocycle also includes heterocyclic radicals that are fused with a carbocyclic radical. Representative examples include, but are not limited to, partially unsaturated condensed heterocyclic groups containing 1 to 5 nitrogen atoms, for example indoline and isoindoline, partially unsaturated condensed heterocyclic groups containing 1 to 2 oxygen atoms and 1 to 3 nitrogen atoms, partially unsaturated condensed heterocyclic groups containing 1 to 2 sulfur atoms and 1 to 3 nitrogen atoms, and saturated condensed heterocyclic groups containing 1 to 2 oxygen or sulfur atoms.

"Heteroaryl" refers to a stable monocyclic, bicyclic, or multicyclic aromatic ring which contains from 1 to 3, or in some embodiments 1, 2, or 3 heteroatoms selected from N, O, S, B, and P (and typically selected from N, O, and S) with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B, or P, with remaining ring atoms being carbon. In one embodiments, the only heteroatom is nitrogen. In one embodiment, the only heteroatom is oxygen. In one embodiment, the only heteroatom is sulfur. Monocyclic heteroaryl groups typically have from 5 to 6 ring atoms. In some embodiments, bicyclic heteroaryl groups are 8- to 10-membered heteroaryl groups, that is groups containing 8 or 10 ring atoms in which one 5-, 6-, or 7-membered aromatic ring is fused to a second aromatic or non-aromatic ring, wherein the point of attachment is the aromatic ring. When the total number of S and O atoms in the heteroaryl group excess 1, these heteroatoms are not adjacent to one another. In one embodiment, the total number of S and O atoms in the heteroaryl group is not more than 2. In another embodiment, the total number of S and O atoms in the heteroaryl group is not more than 1. Examples of heteroaryl groups include, but are not limited to, pyridinyl, imidazolyl, imidazopyridinyl, pyrimidinyl, pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

A "pharmaceutically acceptable salt" is a derivative of the disclosed compound in which the parent compound is modified by making inorganic and organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumption and the quaternary ammonium salts of the parent compound formed, for example, from inorganic or organic salts. Example of such salts include, but are not limited to, those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, mesylic, esylic, besylic, sulfanilic, 2-acetoxybenzoic, fumaric, toluenesulfonic, methanesulfone, ethane disulfonic, oxalic, isethionic, HOOC—$(CH_2)_{1-4}$—COOH, and the like, or using a different acid that produced the same counterion. Lists of additional suitable salts may be found, e.g., in *Remington's Pharmaceutical Sciences*, $17^{th}$ ed., Mack Publishing Company, Easton, PA., p. 1418 (1985).

Compounds of Formula I

The present disclosure provides compounds which are inhibitors of interleukin-1 receptor-associated kinases 1 and 4 (IRAK1 and IRAK4). The presently disclosed compounds have utility in the treatment of medical disorders associated with aberrant expression or signaling of IRAK1 and/or IRAK4, for example inflammatory disorders or cancers.

Thus, in one aspect, a compound of Formula I is provided:

(I)

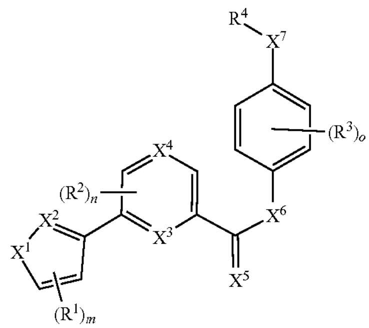

or a pharmaceutically acceptable salt, solvate, or prodrug thereof;

wherein:

$X^1$ is selected from $NR^a$, O, or S;

$X^2$ is selected from N, CH, and $CR^1$;

$X^3$ and $X^4$ are independently selected from N, CH and $CR^2$;

$X^5$ is selected from O, $NR^a$, S, and $CR^bR^c$;

$X^6$ is selected from $NR^a$, —$CR^dR^e$—, S and O;

$X^7$ is a bond or $NR^a$;

$R^a$ is selected from hydrogen, $C_1$-$C_6$alkyl, $C_1$-$C_6$haloalkyl, $C_3$-$C_7$ cycloalkyl, 4- to 10-membered monocyclic or bicyclic heterocycle, 5- to 10-membered monocyclic or bicyclic aryl, or 5- to 10-membered monocyclic or bicyclic heteroaryl, each of which may be optionally substituted with one or more Y groups as allowed by valency;

$R^b$ and $R^c$ are independently selected at each occurrence from hydrogen, halo, nitro, cyano, $C_1$-$C_6$alkyl, $C_1$-$C_6$haloalkyl, $C_3$-$C_7$ cycloalkyl, 4- to 10-membered monocyclic or bicyclic heterocycle, 5- to 10-membered monocyclic or bicyclic aryl, $C(O)R^z$, —$S(O)R^z$, and —$S(O)_2R^z$, each of which may be optionally substituted with one or more Y groups as allowed by valency;

$R^1$, $R^2$ and $R^3$ are independently selected at each occurrence from halo, nitro, cyano, azido, $C_1$-$C_6$alkyl, $C_1$-$C_6$haloalkyl, $C_2$-$C_6$alkenyl, $C_2$-$C_6$alkynyl, $C_3$-$C_7$ cycloalkyl, (4- to 10-membered monocyclic or bicyclic heterocycle)-($C_0$-$C_6$alkyl), (5- to 10-membered monocyclic or bicyclic aryl)-($C_0$-$C_6$alkyl), (5- to 10-membered monocyclic or bicyclic heteroaryl)-($C_0$-$C_6$alkyl), —$OR^x$, —$SR^x$, —$NR^xR^y$, —$C(O)R^z$, —$S(O)R^z$, and —$S(O)_2R^z$, each of which may be optionally substituted with one or more Y groups as allowed by valency;

m is 0, 1, or 2;

n is 0, 1, or 2;

o is 0, 1, 2, 3, or 4;

$R^4$ is selected from

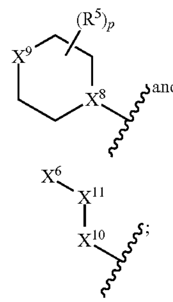

and $X^8$ is selected from N, CH, and $CR^5$;

$X^9$ is selected from S, S(O), and $S(O)_2$;

$R^5$ is independently selected at each occurrence from halo, nitro, cyano, azido, $C_1$-$C_6$alkyl, $C_1$-$C_6$haloalkyl, $C_2$-$C_6$alkenyl, $C_2$-$C_6$alkynyl, $C_3$-$C_7$ cycloalkyl, (4- to 10-membered monocyclic or bicyclic heterocycle)-($C_0$-$C_6$alkyl), (5- to 10-membered monocyclic or bicyclic aryl)-($C_0$-$C_6$alkyl), (5- to 10-membered monocyclic or bicyclic heteroaryl)-($C_0$-$C_6$alkyl), —$OR^x$, —$SR^x$, —$NR^xR^y$, —$C(O)R^z$, —$S(O)R^z$, and —$S(O)_2R^z$, each of which may be optionally substituted with one or more Y groups as allowed by valency;

p is 0, 1, 2, 3, or 4;

$X^{10}$ is $NR^a$;

$X^{11}$ is —$(CR^dR^e)_q$—, wherein q is 1 or 2;

$R^d$ and $R^e$ are independently selected at each occurrence from hydrogen, halo, nitro, cyano, azido, $C_1$-$C_6$alkyl, $C_1$-$C_6$haloalkyl, $C_2$-$C_6$alkenyl, $C_2$-$C_6$alkynyl, $C_3$-$C_7$ cycloalkyl, (4- to 10-membered monocyclic or bicyclic heterocycle)-($C_0$-$C_6$alkyl), (5- to 10-membered monocyclic or bicyclic aryl)-($C_0$-$C_6$alkyl), (5- to 10-membered monocyclic or bicyclic heteroaryl)-($C_0$-$C_6$alkyl), —$OR^x$, —$SR^x$, —$NR^xR^y$, —$C(O)R^z$, —$S(O)R^z$, and —$S(O)_2R^z$, each of which may be optionally substituted with one or more Y groups as allowed by valency;

$R^6$ is selected from —$S(O)_2R^z$;

$R^x$ and $R^y$ are independently selected at each occurrence from hydrogen, $C_1$-$C_6$alkyl, $C_1$-$C_6$haloalkyl, $C_2$-$C_6$alkenyl, $C_2$-$C_6$alkynyl, $C_3$-$C_7$ cycloalkyl, (4- to 10-membered monocyclic or bicyclic heterocycle)-($C_0$-$C_6$alkyl), (5- to 10-membered monocyclic or bicyclic aryl)-($C_0$-$C_6$alkyl), and (5- to 10-membered monocyclic or bicyclic heteroaryl)-($C_0$-$C_6$alkyl), each of which may be optionally substituted with one or more Y groups as allowed by valency;

$R^z$ is independently selected at each occurrence from hydrogen, halo, $C_1$-$C_6$alkyl, $C_1$-$C_6$haloalkyl, $C_2$-$C_6$alkenyl, $C_2$-$C_6$alkynyl, $C_3$-$C_7$ cycloalkyl, (4- to 10-membered monocyclic or bicyclic heterocycle)-($C_0$-$C_6$alkyl), (5- to 10-membered monocyclic or bicyclic aryl)-($C_1$-$C_6$alkyl), (5- to 10-membered monocyclic or bicyclic heteroaryl)-($C_0$-$C_6$alkyl), —$OR^x$, —$SR^x$, and —$NR^xR^y$, each of which may be optionally substituted with one or more Y groups as allowed by valency; and Y is independently selected at each occurrence from halo, hydroxy, amino, cyano, —CHO, —COOH, —$CONH_2$, $C_1$-$C_6$alkyl, $C_2$-$C_6$alkanoyl, (mono or di-$C_1$-$C_6$alkylamino)$C_0$-$C_2$alkyl, $C_1$-$C_6$haloalkyl, hydroxy$C_1$-$C_6$alkyl, ester, carbamate, urea, sulfonamide, —$C_1$-$C_6$alkyl(4- to 10-membered monocyclic or bicyclic heterocycle), —$C_1$-$C_6$alkyl(5- to 10-membered monocyclic or bicyclic heteroaryl), —$C_1$-$C_6$alkyl ($C_3$-$C_7$cycloalkyl), O—$C_1$-$C_6$alkyl($C_3$-$C_7$cycloalkyl), $B(OH)_2$, phosphate, phosphonate, and $C_1$-$C_6$haloalkoxy.

In some embodiments of Formula I, $X^1$ is $NR^a$. In some embodiments of Formula I, $X^1$ is O. In some embodiments of Formula I, $X^1$ is S. In some embodiments of Formula I, $X^1$ is NH.

In some embodiments of Formula I, $X^2$ is N. In some embodiments of Formula I, $X^2$ is CH. In some embodiments of Formula I, $X^2$ is $CR^1$.

In some embodiments of Formula I,

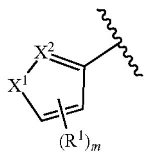

is selected from:

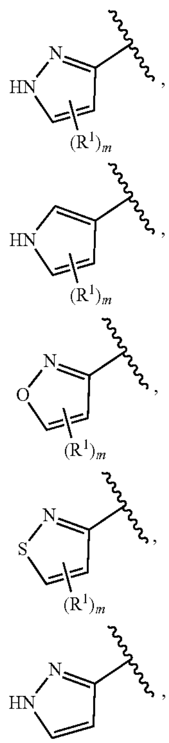

-continued

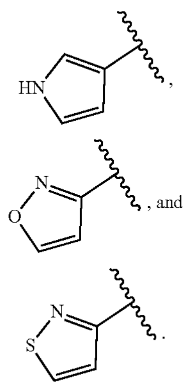

In some embodiments of Formula I, $X^3$ is N. In some embodiments of Formula I, $X^3$ is CH. In some embodiments of Formula I, $X^3$ is $CR^2$.

In some embodiments of Formula I, $X^4$ is N. In some embodiments of Formula I, $X^4$ is CH. In some embodiments of Formula I, $X^4$ is $CR^2$.

In some embodiments of Formula I,

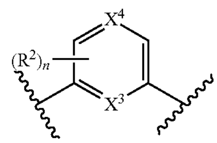

is selected from:

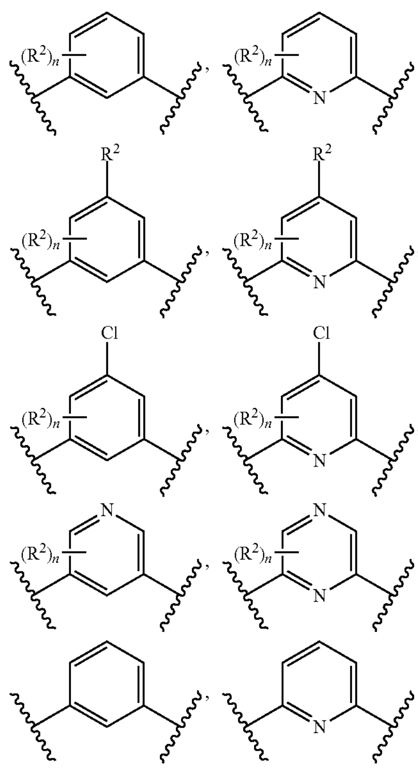

-continued

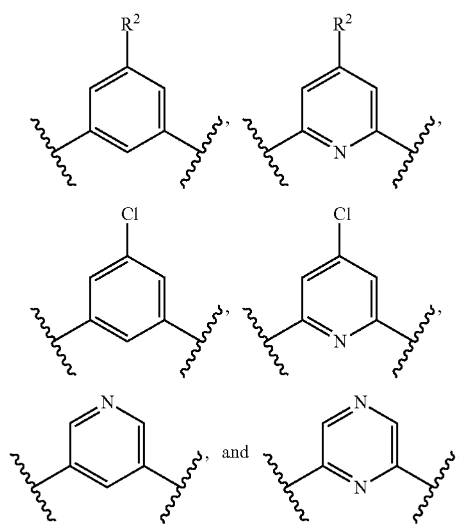

In some embodiments of Formula I, $X^5$ is O. In some embodiments of Formula I, $X^5$ is $NR^a$. In some embodiments of Formula I, $X^5$ is S. In some embodiments of Formula I, $X^5$ is $CR^bR^c$.

In some embodiments of Formula I, $X^6$ $NR^a$. In some embodiments of Formula I, $X^6$ is NH. In some embodiments of Formula I, $X^6$ is O. In some embodiments of Formula I, $X^6$ is —$CR^dR^e$—. In some embodiments of Formula I, $X^6$ is $CH_2$. In some embodiments of Formula I, $X^6$ is S.

In some embodiments of Formula I,

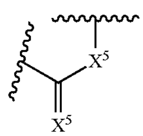

is selected from

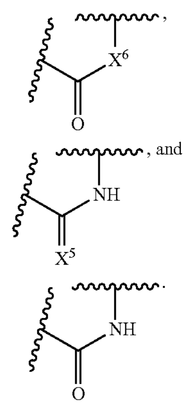

In some embodiments,

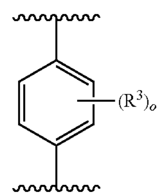

is selected from:

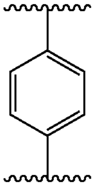
,

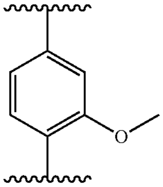
,

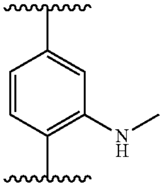
,

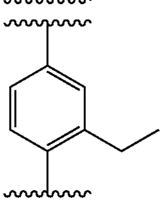
,

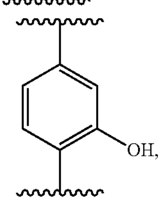
,

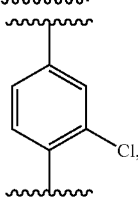
,

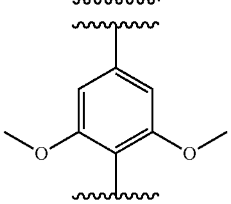
, and

-continued

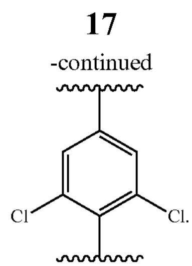

In some embodiments of Formula I, $X^7$ is a bond. In some embodiments of Formula I, $X^7$ is $NR^a$. In some embodiments of Formula I, $X^7$ is NH.

In some embodiments of Formula I, $R^4$ is

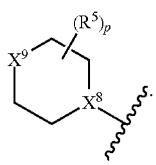

In some embodiments of Formula I, $R^4$ is

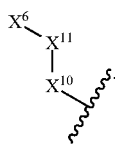

In some embodiments of Formula I,

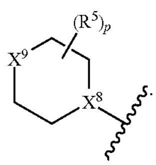

is selected from:

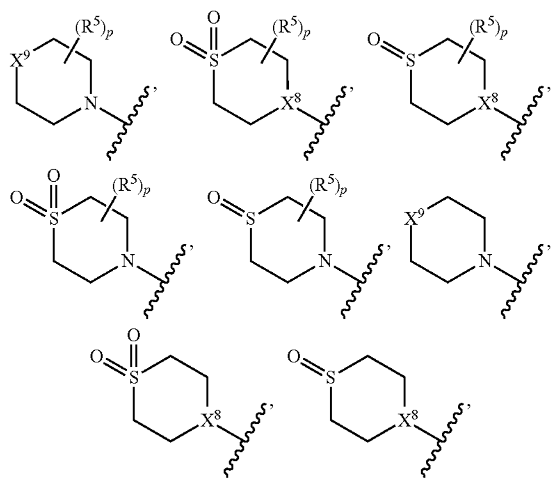

-continued

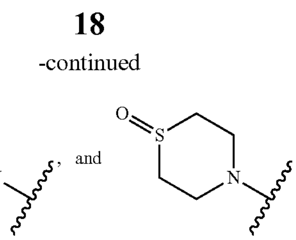

In some embodiments of Formula I,

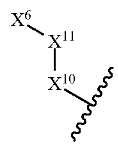

is selected from:

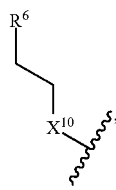

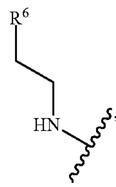

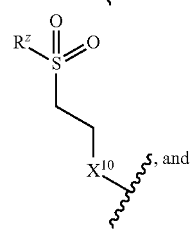

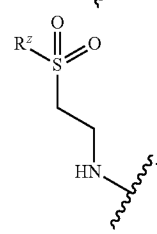

In some embodiments of Formula I, the compound is selected from the group consisting of:

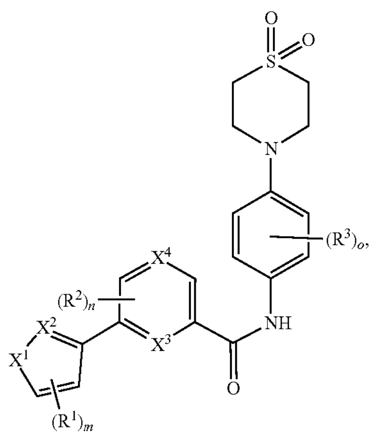
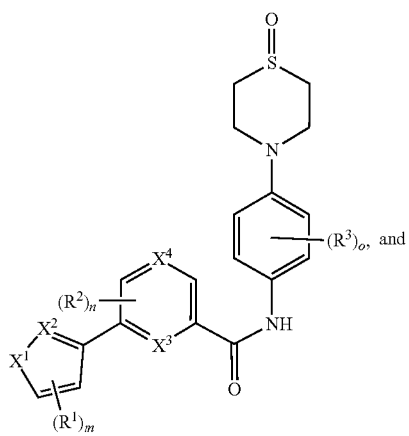
and
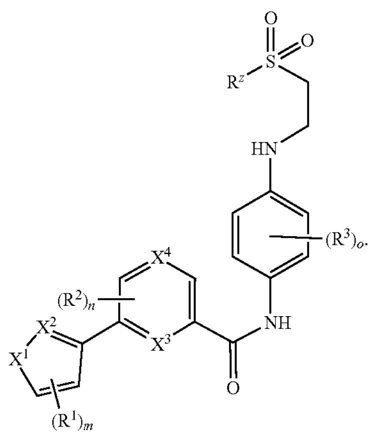
In some embodiments of Formula I, the compound is selected from the group consisting of:
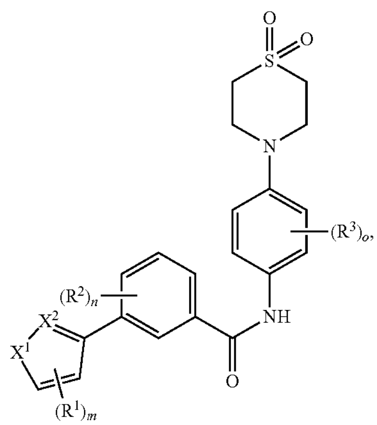
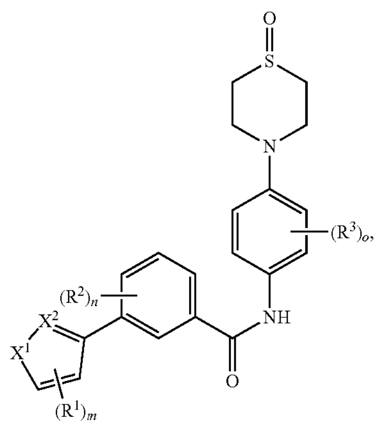
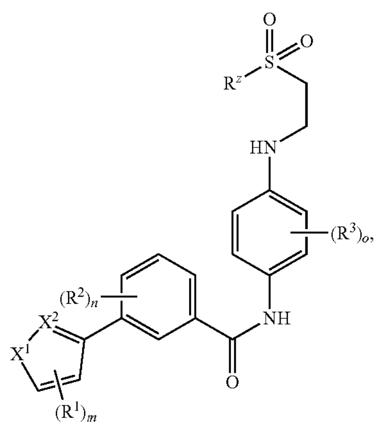
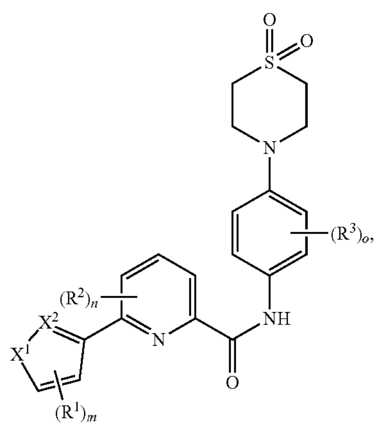

-continued
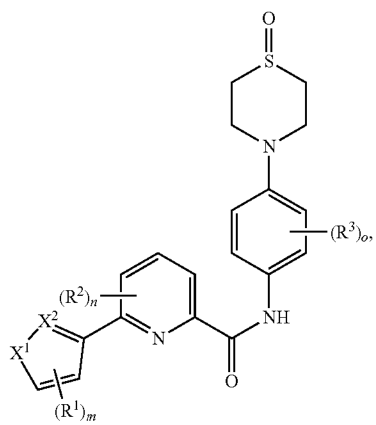
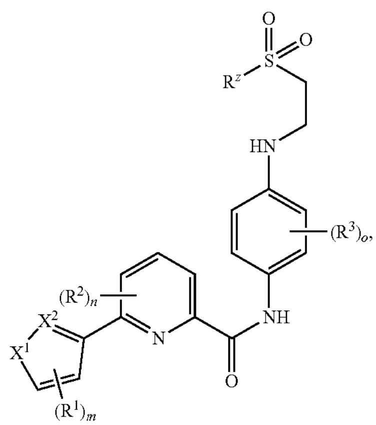
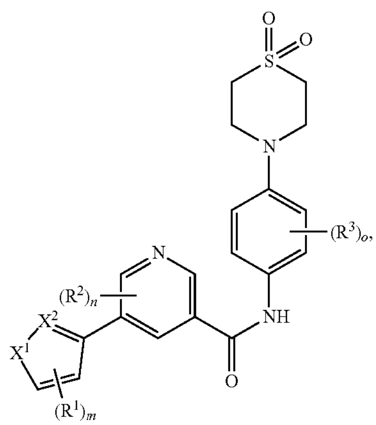
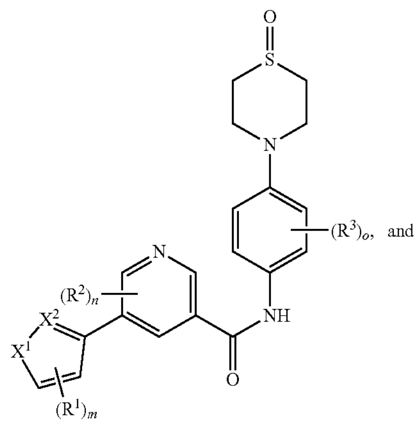
and
-continued
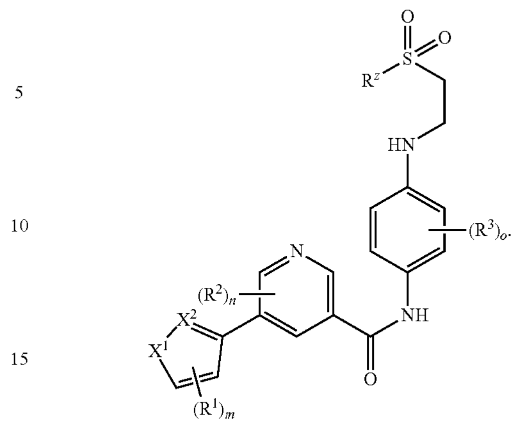
In some embodiments of Formula I, the compound is selected from the group consisting of:
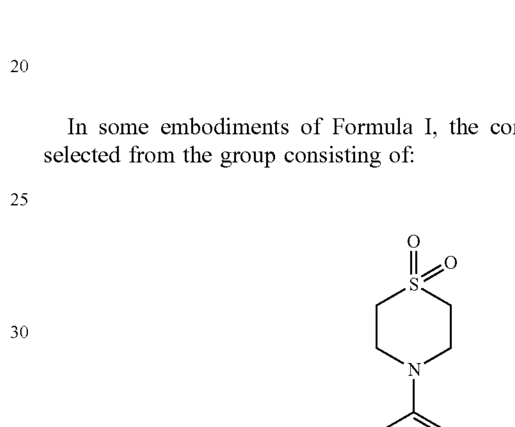
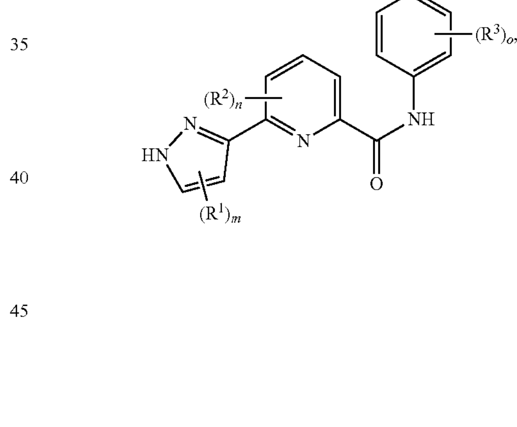
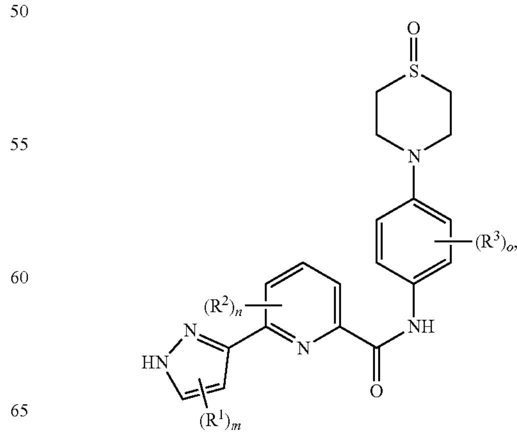

-continued
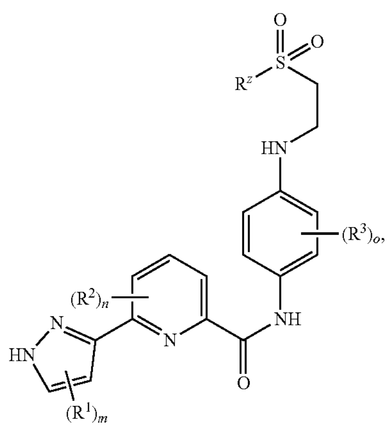
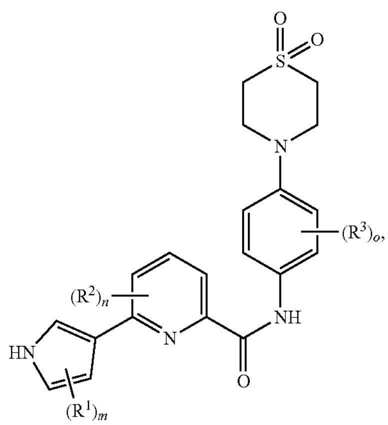
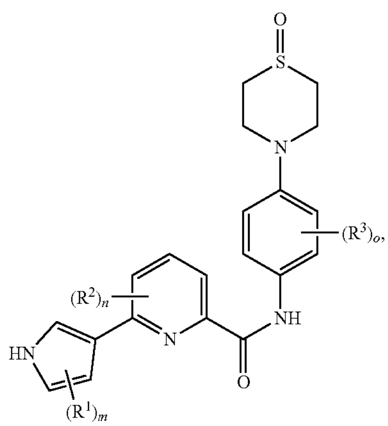
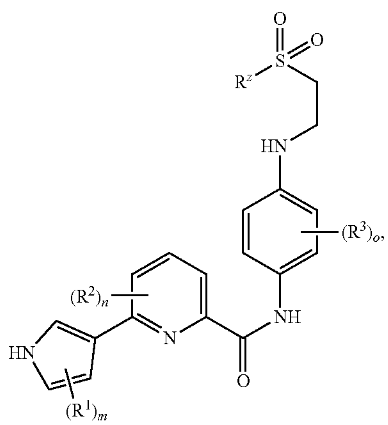
-continued
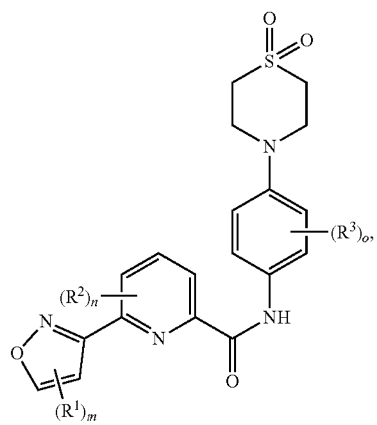
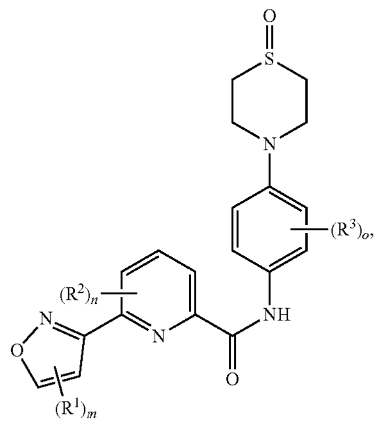
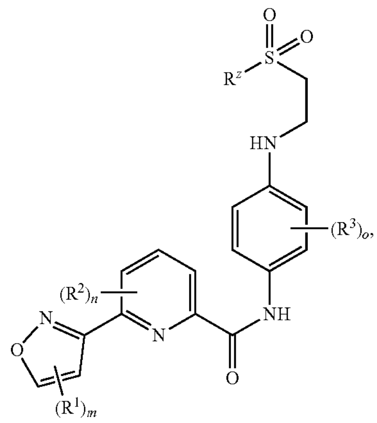
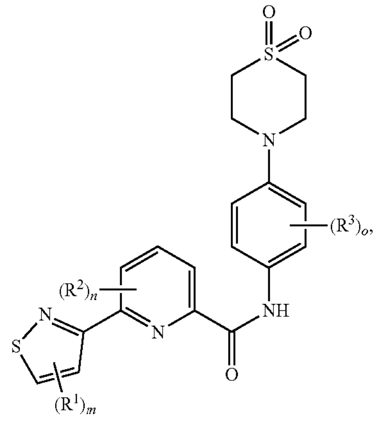

-continued
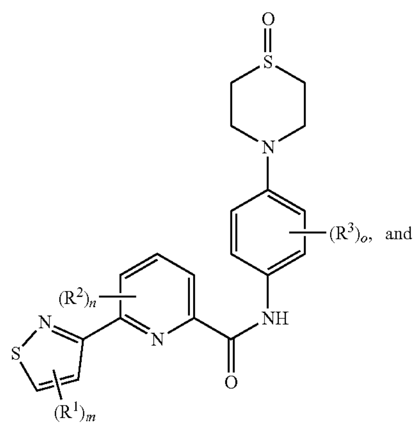
, and
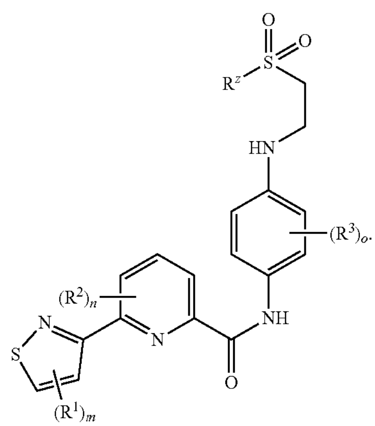
.
Representative examples of compounds of Formula I include, but are not limited to:
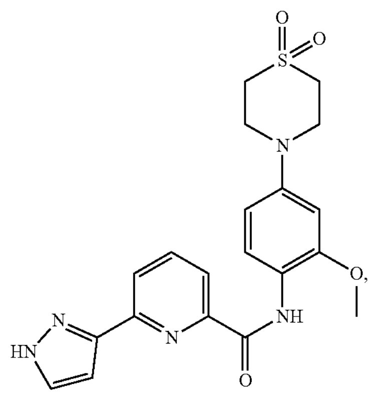
,
-continued
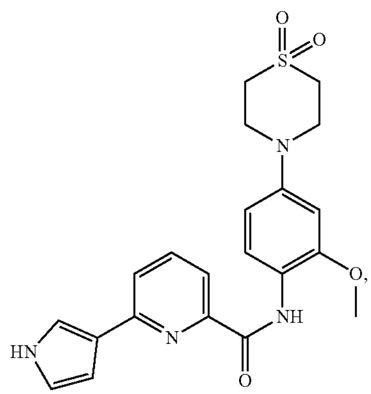
,
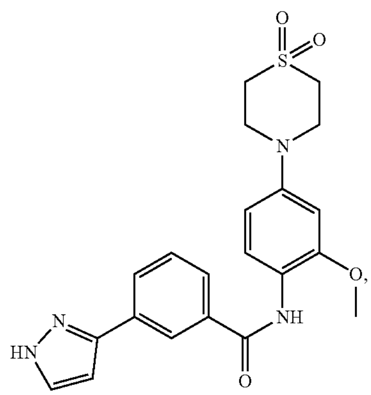
,
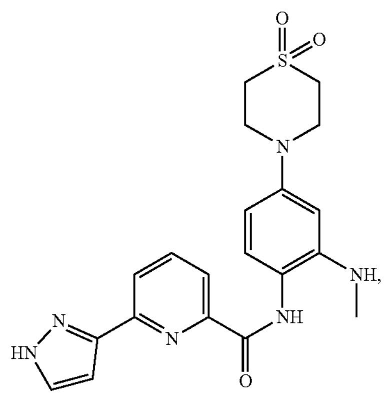
,
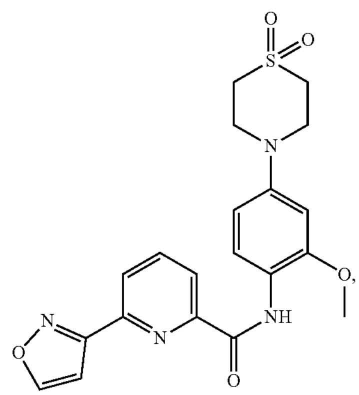
, -continued
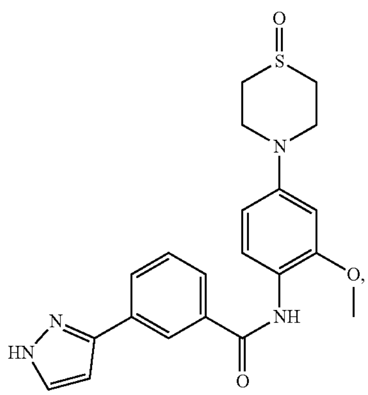
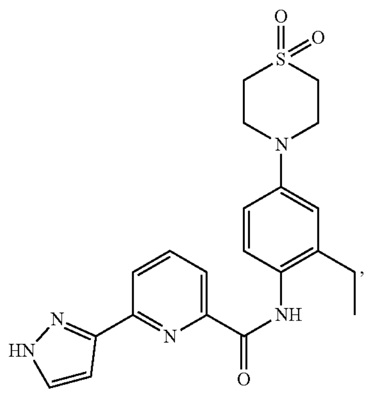
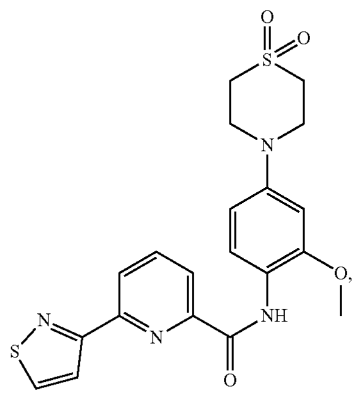
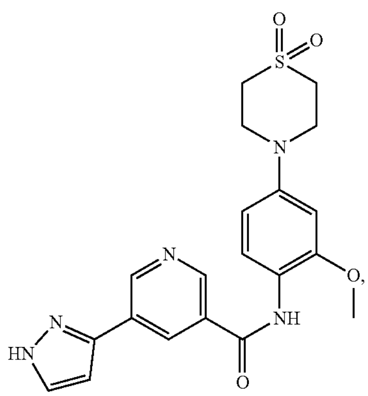
-continued
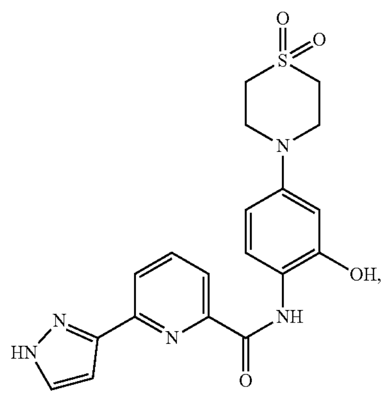
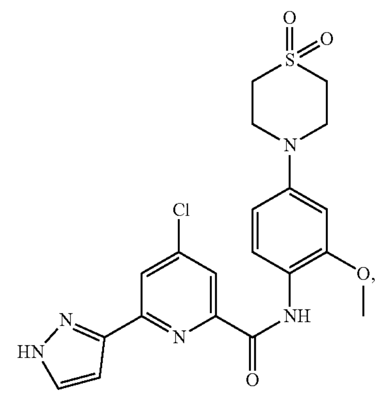
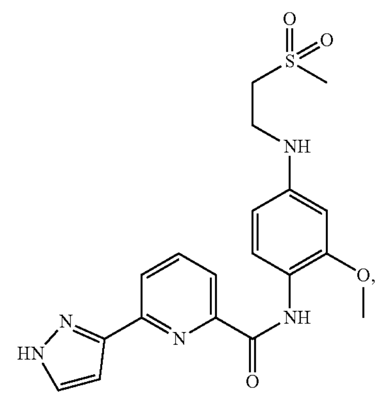
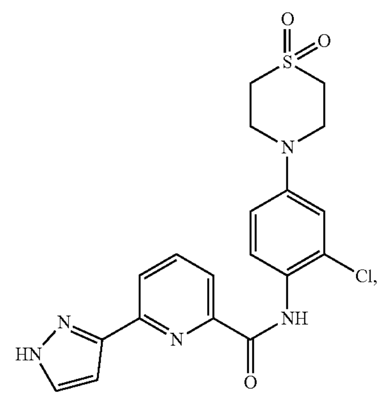

-continued

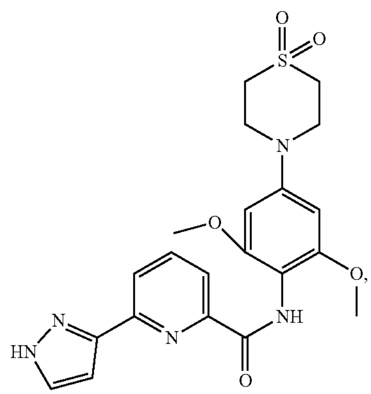

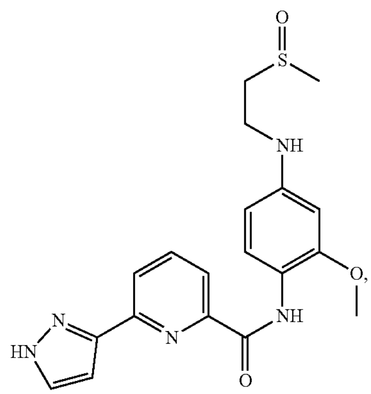

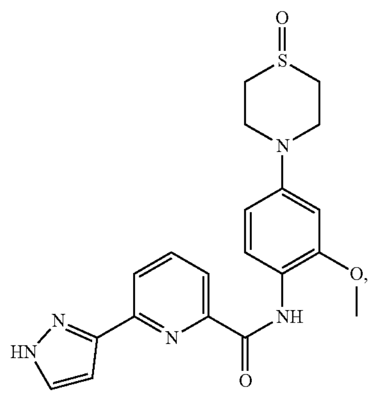

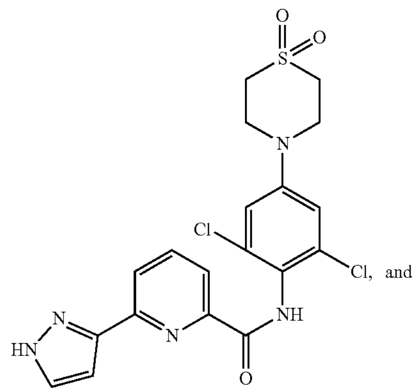

Cl, and

-continued

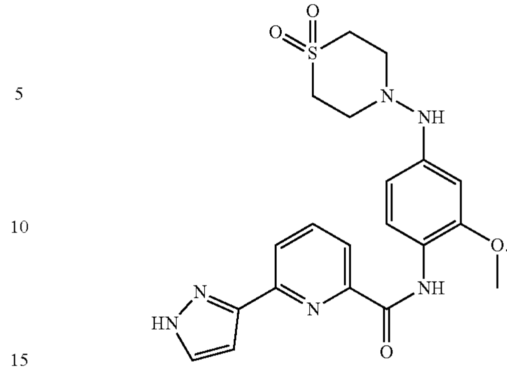

The present disclosure also includes compound of Formula I with at least one desired isotopic substitution of an atom, at an amount above the natural abundance of the isotope, i.e., enriched.

Examples of isotopes that can be incorporated into compounds of the present disclosure include isotopes of hydrogen, carbon, nitrogen, oxygen, phosphorous, fluorine, and chlorine, such as $^{2}H$, $^{3}H$, $^{11}C$, $^{13}C$, $^{15}N$, $^{17}O$, $^{18}O$, $^{18}F$, $^{31}P$, $^{32}P$, $^{35}S$, $^{36}Cl$, and $^{125}I$, respectively. In one embodiment, isotopically labeled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug and substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed herein by substituting a readily available isotopically labeled reagent for a non-isotopically labeled reagent.

By way of general example and without limitation, isotopes of hydrogen, for example deuterium ($^{2}H$) and tritium ($^{3}H$) may optionally be used anywhere in described structures that achieves the desired result. Alternatively or in addition, isotopes of carbon, e.g., $^{13}C$ and $^{14}C$, may be used. In one embodiment, the isotopic substitution is replacing hydrogen with a deuterium at one or more locations on the molecule to improve the performance of the molecule as a drug, for example, the pharmacodynamics, pharmacokinetics, biodistribution, half-life, stability, AUC, Tmax, Cmax, etc. For example, the deuterium can be bound to carbon in allocation of bond breakage during metabolism (an alpha-deuterium kinetic isotope effect) or next to or near the site of bond breakage (a beta-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95, or 99% or more enriched in an isotope at any location of interest. In some embodiments, deuterium is 80, 85, 90, 95, or 99% enriched at a desired location. Unless otherwise stated, the enrichment at any point is above natural abundance, and in an embodiment is enough to alter a detectable property of the compounds as a drug in a human.

The compounds of the present disclosure may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a disclosed compound and water. Pharmaceutically acceptable solvates in accordance with the invention include those wherein the solvent of crystallization may be isotopically substituted, e.g., $D_2O$, d6-acetone, or d6-DMSO. A solvate can be in a liquid or solid form.

A "prodrug" as used herein means a compound which when administered to a host in vivo is converted into a parent drug. As used herein, the term "parent drug" means any of the presently described compounds herein. Prodrugs can be used to achieve any desired effect, including to enhance properties of the parent drug or to improve the pharmaceutic or pharmacokinetic properties of the parent, including to increase the half-life of the drug in vivo. Prodrug strategies provide choices in modulating the conditions for in vivo generation of the parent drug. Non-limiting examples of prodrug strategies include covalent attachment of removable groups, or removable portions of groups, for example, but not limited to, acylating, phosphorylation, phosphonylation, phosphoramidate derivatives, amidation, reduction, oxidation, esterification, alkylation, other carboxy derivatives, sulfoxy or sulfone derivatives, carbonylation, or anhydrides, among others. In certain embodiments, the prodrug renders the parent compound more lipophilic. In certain embodiments, a prodrug can be provided that has several prodrug moieties in a linear, branched, or cyclic manner. For example, non-limiting embodiments include the use of a divalent linker moiety such as a dicarboxylic acid, amino acid, diamine, hydroxycarboxylic acid, hydroxyamine, di-hydroxy compound, or other compound that has at least two functional groups that can link the parent compound with another prodrug moiety, and is typically biodegradable in vivo. In some embodiments, 2, 3, 4, or 5 prodrug biodegradable moieties are covalently bound in a sequence, branched, or cyclic fashion to the parent compound. Non-limiting examples of prodrugs according to the present disclosure are formed with: a carboxylic acid on the parent drug and a hydroxylated prodrug moiety to form an ester; a carboxylic acid on the parent drug and an amine prodrug to form an amide; an amino on the parent drug and a carboxylic acid prodrug moiety to form an amide; an amino on the parent drug and a sulfonic acid to form a sulfonamide; a sulfonic acid on the parent drug and an amino on the prodrug moiety to form a sulfonamide; a hydroxyl group on the parent drug and a carboxylic acid on the prodrug moiety to form an ester; a hydroxyl on the parent drug and a hydroxylated prodrug moiety to form an ester; a phosphonate on the parent drug and a hydroxylated prodrug moiety to form a phosphonate ester; a phosphoric acid on the parent drug and a hydroxylated prodrug moiety to form a phosphate ester; a hydroxyl on the parent drug and a phosphonate on the prodrug to form a phosphonate ester; a hydroxyl on the parent drug and a phosphoric acid prodrug moiety to form a phosphate ester; a carboxylic acid on the parent drug and a prodrug of the structure $HO—(CH_2)_2—O—(C_{2-24}$ alkyl) to form an ester; a carboxylic acid on the parent drug and a prodrug of the structure $HO—(CH_2)_2—S—(C_{2-24}$ alkyl) to form a thioester; a hydroxyl on the parent drug and a prodrug of the structure $HO—(CH_2)_2—O—(C_{2-24}$ alkyl) to form an ether; a hydroxyl on the parent drug and a prodrug of the structure $HO—(CH_2)_2—O—(C_{2-24}$ alkyl) to form an thioether; and a carboxylic acid, oxime, hydrazide, hydrazine, amine or hydroxyl on the parent compound and a prodrug moiety that is a biodegradable polymer or oligomer including but not limited to polylactic acid, polylactide-co-glycolide, polyglycolide, polyethylene glycol, polyanhydride, polyester, polyamide, or a peptide.

In some embodiments, a prodrug is provided by attaching a natural or non-natural amino acid to an appropriate functional moiety on the parent compound, for example, oxygen, nitrogen, or sulfur, and typically oxygen or nitrogen, usually in a manner such that the amino acid is cleaved in vivo to provide the parent drug. The amino acid can be used alone or covalently linked (straight, branched or cyclic) to one or more other prodrug moieties to modify the parent drug to achieve the desired performance, such as increased half-life, lipophilicity, or other drug delivery or pharmacokinetic properties. The amino acid can be any compound with an amino group and a carboxylic acid, which includes an aliphatic amino acid, alkyl amino acid, aromatic amino acid, heteroaliphatic amino acid, heteroalkyl amino acid, heterocyclic amino acid, or heteroaryl amino acid.

Methods of Treatment

In one aspect, methods are provided for the treatment of medical disorders associated with aberrant expression or signaling of IRAK4.

In some embodiments, methods are provided for the treatment of an inflammatory disorder in a subject in need thereof comprising administering a therapeutically effective amount of a compound disclosed herein to the subject, or a pharmaceutically acceptable salt, solvate or prodrug thereof. Representative examples of inflammatory disorders include peritonitis, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, atopic dermatitis, graft vs. host disease, osteoporosis, multiple myeloma-related bone disorder, leukemias and related disorders, myelodysplastic syndrome, acute myelogenous leukemia, clonal hematopoiesis, anemia of chronic diseases, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, neurological damage due to stroke, ulcerative colitis, infectious hepatitis, juvenile diabetes, lichen planus, acute dermatomyositis, eczema, primary cirrhosis, uveitis, Behcet's disease, atopic skin disease, pure red cell aplasia, aplastic anemia, amyotrophic lateral sclerosis, nephrotic syndrome, burns, bronchitis, tendinitis, bursitis, periarteritis nodosa, thyroiditis, Hodgkin's disease, rheumatic fever, sarcoidosis, polymyositis, gingivitis, hypersensitivity, conjunctivitis, swelling occurring after injury, allergic rhinitis, endotoxin shock syndrome, and atherosclerosis, psoriatic arthritis, vasculitis, Polymyalgia, Rheumatica, Wegener's granulomatosis, temporal arteritis, chronic obstructive pulmonary disease, cryoglobulinemia, transplant rejection, inflammatory ocular diseases, and ataxia telangiectasia.

In another aspect, methods are provided for the treatment of organ fibrosis in a subject in need thereof comprising administering a therapeutically effective amount of a compound disclosed herein to the subject, or a pharmaceutically acceptable salt, solvate, or prodrug thereof. Representative examples of organ fibrosis which may be treated include renal fibrosis, pulmonary fibrosis, cirrhosis, endomyocardial fibrosis, Crohn's disease, liver fibrosis, heart fibrosis, scleroderma, or progressive massive fibrosis.

Malignancies that can be treated using the compounds of the present disclosure include ovarian, fallopian tube, primary peritoneal, endometrial and uterine cancers, including all histologic sub types associated with the same, such as, but not limited to serous, endometrioid, clear cell, mucinous, undifferentiated, poorly differentiated, carcinosarcoma (MMMT), sarcoma germ cell tumors, and sex cord stromal tumors.

Carcinomas intended for treatment with the methods of this invention include, but not limited to, acinar carcinoma, acinous carcinoma, alveolar adenocarcinoma, carcinoma adenomatosum, adenocarcinoma, carcinoma of adrenal cortex, alveolar carcinoma, alveolar cell carcinoma, basal cell carcinoma, carcinoma basocellular, basaloid carcinoma, basosquamous cell carcinoma, breast carcinoma, bronchioalveolar carcinoma, bronchiolar carcinoma, cerebriform carcinoma, cholangiocellular carcinoma, chorionic carcinoma, colloid carcinoma, comedocarcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliate adenoids, carcinoma exulcere, carcinoma fibrosum, gelatinform carcinoma, gelatinous carcinoma, giant cell carcinoma, gigantocellulare, glandular carcinoma, granulose cell carcinoma, hair matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lentivular carcinoma, carcinoma lenticulare, lipomatous carcinoma, lymphoepithelial carcinoma, carcinoma mastotoids, carcinoma medullare, medullary carcinoma, carcinoma melanodes, melanotonic carcinoma, mucinous carcinoma, carcinoma muciparum, carcinoma mucocullare, mucoepidermoid carcinoma, mucous carcinoma, carcinoma myxomatodes, masopharyngeal carcinoma, carcinoma nigrum, oat cell carcinoma, carcinoma ossificans, osteroid carcinoma, ovarian carcinoma, papillary carcinoma, periportal carcinoma, preinvasive carcinoma, prostate carcinoma, renal cell carcinoma of kidney, reserve cell carcinoma, carcinoma sarcomatodes, scheinderian carcinoma, scirrhous carcinoma, carcinoma scrota, signet-ring cell carcinoma, carcinoma simplex, small cell carcinoma, solandoid carcinoma, pancreatic, breast, melanoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberrosum, tuberous carcinoma, verrucous carcinoma, carcinoma vilosum.

The invention also provides methods and agents to treat sarcomas. Sarcomas are mesenchymal neoplasms that arise in bone and soft tissues. Different types of sarcomas are recognized and these include: liposarcomas (including myxoid liposarcomas and pleomorphic liposarcomas), leiomyosarcomas, rhabdomyosarcomas, neurofibrosarcomas, malignant peripheral nerve sheath tumors, Ewing's tumors (including Ewing's sarcoma of bone, extraskeletal or non-bone) and primitive neuroectodermal tumors (PNET), synovial sarcoma, hemangioendothelioma, fibrosarcoma, desmoids tumors, dermatofibrosarcoma protuberance (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) and osteosarcoma (also known as osteogenic sarcoma) skeletal and extra-skeletal, and chondrosarcoma.

Optionally, the cancers to be treated are a refractory or a responding cancer.

In another important aspect, compounds of his invention can also be used to treat cancers that are immunogenic. Examples of immunogenic cancers include malignant melanoma and renal cell carcinoma, mantel cell lymphoma, follicular lymphoma, diffuse large B-cell lymphoma, T-cell acute lymphoblastic leukemia, Burkitt Lymphoma, myeloma, immunocytoma, acute promyelocyte leukemia, chronic myeloid/acute lymphoblastic leukemia, acute leukemia, B-cell acute lymphoblastic leukemia, anaplastic large cell leukemia, myelodysplasia syndrome/acute myeloid leukemia, non-Hodgkin's lymphoma, chronic lymphocytic leukemia, acute myelogenous leukemia (AML), common (pre-B)acute lymphocytic leukemia, malignant melanoma, T-cell lymphoma, leukemia, B-cell lymphoma, epithelial malignancies, lymphoid malignancies, gynecologic carcinoma, biliary adenocarcinomas and ductal adenocarcinomas of the pancreas.

The present disclosure also provides a method for inhibiting angiogenesis in a subject comprising administering a therapeutically effective amount of a compound disclosed herein, or a pharmaceutically acceptable salt, solvate or prodrug thereof. Angiogenesis, the rapid proliferation of epithelial cells resulting in formation of new blood vessels, supports the progression and survival of tumors. As a secondary effect, angiogenesis may damage the various organs and tissues, eyes, skin, heart, blood vessels, lung, GI tract and genitourinary tract. Methods and techniques to assess angiogenesis are known to those of ordinary skill in the art.

Also provided are methods for suppressing tumor cell growth in a subject in need thereof comprising administering a therapeutically effective amount of a compound described herein, or a pharmaceutically acceptable salt thereof.

Also provided are method for sensitizing a tumor to treatment with an additional therapeutic agent comprising administering a therapeutically effective amount of a compound described herein, or a pharmaceutically acceptable salt thereof, solvate or prodrug thereof.

In another aspect, a method is provided for IL1b-induced activation of NF-κB in a subject in need thereof comprising administering to the subject a therapeutically effective amount of a compound described herein, or a pharmaceutically acceptable salt, solvate, or prodrug thereof.

In another aspect, a method is provided for stem cell mobilization and/or stem cell engraftment in a subject upon administration with agents mentioned herein, alone or in combination with additional therapeutic agents.

In another aspect, a method is provided for treating a pain disorder in a subject in need thereof comprising administering a therapeutically effective amount of a compound described herein, or a pharmaceutically acceptable salt, solvate or prodrug thereof. Representative examples of pain disorders which may be treated include, but are not limited to, inflammatory pain (including infection-induced inflammatory pain including but not limited to pain induced from the flu, SARS, or a cold), post-operative pain, osteoarthritis, pain associated with metastatic cancer, trigeminal neuralgia, acute herpetic and post-herpetic neuralgia, diabetic neuropathy, causalgia, brachial plexus avulsion, occipital neuralgia, reflex sympathetic dystrophy, fibromyalgia, gout, and phantom limb pain.

In some embodiments, the pain disorder comprises neuropathic or nociceptive pain. Neuropathic pain is pain caused by damage or disease that affects the somatosensory nervous system. Neuropathic pain is typically characterized by abnormal sensations (dysethesia) or pain from normally non-painful stimuli (allodynia). Neuropathic pain may result from a disorder of the peripheral system or a disorder of the central nervous system, e.g, the brain or spinal cord. Central neuropathic pain is found in cases of spinal cord injury, multiple sclerosis, and stroke. Peripheral neuropathic pain can be found in patients with diabetes (diabetic neuropathy), herpes zoster infection, HIV infection, nutritional deficiencies, exposure to toxins, remote manifestations of malignancies, immune-mediated disorders, and physical trauma to the nerve trunk. Neuropathic pain may occur in cases of cancer either due to direct compression of a tumor on peripheral nerves, or as a side effect of chemotherapy (chemotherapy-induced peripheral neuropathy), radiation or surgery.

The compounds as described herein may be administered in combination with other therapies such as, for example, radiation therapy, surgery, conventional chemotherapy, one or more checkpoint inhibitors, or with a combination of one or more additional therapies.

For example, the compounds described herein can be administered before, after, or simultaneously with chemotherapeutic and/or cytotoxic agents. Simultaneous administration can take place in the form of one fixed combination with two or more active ingredients, or by simultaneously administering two or more compounds that are formulated independently. The chemotherapeutic and/or cytotoxic agents which may be administered include, but are not limited to, alkylating agents (e.g., chlorambucil, cyclophosphamide, ccnu, melphalan, procarbazine, thiotepa, bcnu, and busulfan), antimetabolites (e.g., 6-mercaptopurine and 5-fluorouracil), anthracyclines (e.g., daunorubicin, doxorubicin, idarubicin, epirubicin, and mitoxantrone), antitumor antibiotics (e.g., bleomycin), monoclonal antibodies (e.g., alemtuzumab, bevacizumab, cetuximab, gemtuzumab, ibritumomab, panitumumab, rituximab, tositumomab, and trastuzumab), platinums (e.g., cisplatin, oxaliplatin, and carboplatin), plant alkaloids (e.g., vincristine), topoisomerase I or II inhibitors (e.g., irinotecan, topotecan, amsacrine, etoposide, etoposide phosphate, and teniposide), vinca alkaloids (e.g., vincristine, vinblastine, vinorelbine, and vindesine), taxanes (e.g; paclitaxel and docetaxel), epipodophyllotoxins (e.g., etoposide and teniposide), nucleoside analogs, and angiogenesis inhibitors (e.g., Avastin (beracizumab), a humanized monoclonal antibody specific for VEGF-A). Examples of glutathione antagonists include but are not limited to buthionine sulfoximine, cyclophosphamide, ifosphamide, actinomycin-d and N-(4-hydroxyphenyl) retinamide (4-HPR). Examples of angiogenesis inhibitors include but are not limited to 2-methoxyestradiol (2-ME), AG3340, Angiostatin, antithrombin-III, Anti-VEGF antibody, Batimastat, bevacizumab (Avastin), BMS-275291, CA1, Canstatin, combretastatin, Combretastatin-A4 phosphate, CC-5013, captopril, celecoxib, Dalteparin, EMD121974, Endostatin, Erlotinib, Gefitinib, Genistein, Halofuginone, ID 1, ID3, IM862, Imatinib mesylate, Inducible protein-10, Interferon-alpha, Interleukin-12, Lavendustin-a, LY317615, or AE-941, Marimastat, Mapsin, Medroxyprogesterone acetate, Meth-1, Meth-2, Neovastat, Osteopontin cleaved product, PEX, Pigment epithelium growth factor (PEGF), platelet growth factor 4, prolactin fragment, proliferin-related protein (PRP), PTK787/ZK222584, recombinant human platelet factor-4(rPF4), restin, squalamine, SU5416, SU6668, Suramin, Taxol, Tecogalan, Thalidomide, Tetrathiomolybdate (TM), Thrombospondin, TNP-470, Troponin I, Vasostatin, VEGF1, VEGF-TPvAP and ZD6474. In some embodiment the angiogenesis inhibitor is a VRGF antagonist. The VEGF antagonist may be a VEGF binding molecule. VEGF binding molecule include VEGF antibodies, or antigen binding fragment (s) thereof. One example of a VEGF antagonist is NeXstar.

Chemotherapeutic agents that can be combined with the compounds disclosed herein include, but are not limited to, DNA damaging agents and these include topoisomerase inhibitors (e.g., etoposide, camptothecin, topotecan, irinotecan, teniposide, mitoxantrone), anti-microtubule agents (e.g., vincristine, vinblastine), antimetabolite agents (e.g., cytarabine, methotrexate, hydroxyurea, 5-fluorouracil, flouridine, 6-thioguanine, 6-mercaptompurine, fludarabine, pentostatin, chlorodeoxyadenosine), DNA alkylating agents (e.g., cisplatin, mecholorethamine, cyclophosphamide, ifosphamide, melphalan, chlorambucil, busulfan, thiotepa, carmustine, lomustine, carboplatin, dacarbazine, procarbazine) and DNA strand break inducing agents (e.g., bleomycin, doxorubicin, daunorubicin, idarubicin, mitomycin C).

Other chemotherapeutic agents that can be combined with the compounds described herein include: synthetic, semisynthetic and naturally derived agents. Important chemotherapeutic agents include, but are not limited to, Avicine, Aclarubicin, Acodazole, Acronine, Adozelesin, Adriamycin, aldesleukin, Alitretinoin, AUopurinol sodium, Altretamine, Ambomycin, Ametantrone acetate, Aminoglutethimide, Amsacrine, Anastrazole, Annonaceous Acetogenins, Anthramycin, Asimicin, Asparaginase, asperlin, Azacitidine, azetepa, Azotomycin, batimastat, benzodepa, bexarotene, Bicalutamide, Bisantrene, Bisnafide, Bizelesin, B leomycin, Brequinar, Bropirimine, Bullatacin, Busulfan, Cabergoline, cactinomycin, calusterone, caracemide, carbetimer, carboplatin, carmustine, carubicin, carzelesin, cedefingol, chlorambucil, celecoxib, cirolemycin, cisplatin, cladribine, crisnatol, cyclophosphamide, cytarabine, dacarbazine, DACA, dactinomycin, Daunorubicin, daunomycin, Decitabine, denileukin, Dexormaplatin, Dezaguanine, Diaziquone, Docetaxel, Doxorubicin, Droloxifene, Dromostalone, Duazomycin, Edatrexate, Eflornithine, Elsamitrucin, Estramustine, Etanidazole, Etoposide, Etoprine, Fadrozole, Fazarabine, Fenretinide, Floxuridine, Fludarabine, Fluorouracil, Flurocitabine, 5-FdUMP, Fosquidone, Fosteuecine, FK-317, FK-973, FR-66979, FR-900482, Gemcitabine, Gemtuzumab, Ozogamicin, Gold Aul 98, Goserelin, Guanacone, Hydroxyurea, Idarubicin, Ilmofosine, Interferon alpha and analogs, Iproplatin, irinotecan, Lanreotide, Letrozole, Leuprolide, Liarozole, Lometrexol, Lomustine, Losoxantrone, masoprocol, Maytansine, Mechlorethamine, Megestrol, Melengestrol, Melphalan, Menogaril, Metoprine, maturedepa, mitindomide, Mitocarcin, Mitogillin, Mitomalacin, Mitomycin, Mitomycin C, Mitosper, Mitotane, Mitoxantrone, Mycophenolic acid, Nocodazole, Nogalamycin, Oprelvekin, ormaplatin, Oxisuran, Paclitaxel, pamidronate, pegaspargase, Peliomycin, Pentamustine, Peplomycin, Perfosfamide, Pipobroman, Piposulfan, Piroxantrone, Plicamycin, Plomestane, Porfimer, Porfiromycin, Prednimustine, procarbazine, Puromycin, Pyrazofurin, Riboprine, Rituximab, Rogletimide, Rolliniastatin, safingol, Samarium, Semustine, Simtrazene, Sparfosate, Sparsomycin, spirogermanium, Spiromustine, Spiroplatin, Squamocin, Squamotacin, streptonigrin, streptozocin, SrC12, Sulphofenur, Talisomycin, Taxane, Toxoid, Tecoglan, Tegafur, teloxantrone, Temoporfin, teniposide, Teroxirone, Testolactone, Thiamiprine, Thiotepa, Thymitaq, Tiazofurin, Tirapazamine, Tomudex, Top-53, Topotecan, Toremixifme, Trastuzumab, Trestolone, triciribine, Triciribine, Trimetrexate, trimetrexate glucuronate, Triptorelin, Tubulozole, uracil mustard, Uredepa, valrubicin, vapreotide, Vinblastine, Vincristine, Vindesine, Vinepidine, Vinglycinate, Vinleurosine, Vinorelbine, Vinrosidine, Vinzolidine, Vorozole, Zeniplatin, Zino statin, Zorubicin, 2-cholrodeoxyrubicine, 2'-deoxyformycin, 9-aminocamptothecin, raltitrexed, N-propargyl-5,8-didezafolic acid, 2-cholo-2'arabinofluoro-T deoxyadenosine, 2-cholo-2'-deoxyadenosine, anisomycin, Trichostatin, hPRL-G129R, CEP-751, Linomide, Sulfur mustard, nitrogen mustard, N-methyl-N-nitrosourea, fotemustine, Streptozotocin, dacarbazine, mitozolomide, temozolomide, AZQ, ormaplatin, CI-973, DWA21 14R, JM216, JM335, Bisplatinum, Tomudex, azacitidine, cytrabincine, gemcitabine, 6-mercaptopurine, Hypoxanthine, Teniposide, CPT-11, Doxorubicin, Daunorubicin, Epirubicin, darubicin, losoxantrone, amsacrine, pyrazoloacridine, all trans retinol, 14-hydroxy-retro-retinol, all-trans retinoic acid, N-(4-hydroxyphenyl) retinamide, 13-cisretinoic acid, 3-methyl TTNEB, 9-cisretenoic acid, fludarabine, and 2-Cda.

Other chemotherapeutic agents that can be combined with the compounds described herein include: 20-epi1,25-dihydroxyvitamin-D3, 5-ethynyl uracil, abiraterone, aclarubicin, acylfulvene, adecylpenol, adozelesin, aldesleukin, ALL-TK antagonists, altretamine, ambumastine, amidox, amifostine, amino levulinic acid, anagrelide, anastrozole, andrographolide, angiogenesis inhibitors, antagonist D, antagonists D, antarelix, anti-dorsalizing morphogenetic protein-1, antiandrogen, antiestrogen, antineoplastone, antisense oligonucleotides, aphidicolin, apoptosis gene modulators, apoptosis regulators, apurinic acid, ara-cdp-dl-PTBA, arginine aminase, asulacrine, atamestine, atrimustine, axinamastine 1 and axinamastine 2, axinamastine 3, azasetron, azatoxin, azatyrosine, baccatin III derivatives, balanol, BCR/ABL antagonist, benzochlorins, benzoylsaurosporine, beta lactam derivatives, beta-alethine. Perillyl alcohol, phenozenomyein, phenyl acetate, phosphatase inhibitors, picibanil, pilocarbine and salts or analogs thereof, pirarubicin, piritrexim, placetin A, placetin B, plasminogen activator inhibitor, platinum complex, phenyl ethyl isothiocyanate and analogs thereof, platinum compounds, platinum triamine complex, podophylotoxin, porfimer sodium, porphyromycin, propyl bis acridones, prostaglnadins J2, protease inhibitors, protein A based immune modulators, PKC inhibitors, microalgal, protein tyrosine phosphatase inhibitors, purine nucleoside phosphorylase inhibitors, purpurins, pyrazoloacridines, pyridoxylated haemoglobin polyoxyethylene conjugate, raf antagonists, raltitrexed, ramosetron, ras farnesyl protein tranaferase inhibitors, rasinhibitors, ras-GAP inhibitors, ratellitptine demethylated, Rhenium Re 186 etidronate, rhizoxine, ribozyme, RII retinide, rogletimide, rosagliatazone and analogs and derivatives thereof, rohitukine, romurtide, roquinimex, rubiginone B1, ruboxyl, safingol, saintopin, SarCNU, sarcophytol A, sargrmostim, sdi 1 mimetics, semustine, senescence derived inhibitor 1, sense oligonucleotide, signal transduction inhibitors, signal transduction modulators, single chain antigen binding protein, sizofiran, sobuzoxane, sodium borocaptate, sodium phenyl acetate, solverol, somatomedin binding protein, sonermin, sparfosic acid, spicamycin D, spiromustin, splenopentine, spongistatin 1, squalamine, stem cell inhibitor, stem cell division inhibitor, stipiamide, stromelysin, sulfinosine, superactive vasoactive intestinal peptide antagonists, suradista, siramin, swainsonine, synthetic glycosaminoglycans, tallimustine, tamoxifen methiodide, tauromustine, tazarotene, tacogalan sodium, tegafur, tellurapyrilium, telomerase inhibitors, temoporfin, tmeozolomide, teniposide, tetrachlorodecaoxide, tetrazomine, thaliblastine, thalidomide, thiocoraline, thrombopoetin and mimetics thereof, thymalfasin, thymopoetin receptor agonist, thymotrinan, thyroid stimulating harmone, tin ethyl etiopurpin, tirapazamine, titanocene and salts thereof, topotecan, topsentin, toremifene, totipotent stem cell factors, translation inhibitors, tretinoin, triacetyluridine, tricribine, trimetrexate, triptorelin, tropisetron, turosteride, tyrosine kinase inhibitors, tyrphostins, UBC inhibitors, ubenimex, urogenital sinus derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozol, zanoterone, zeniplatin, zilascorb and zinostatin.

Further chemotherapeutic agents that can be combined with the compounds described herein include: antiproliferative agents (e.g., piritrexim isothiocyanate), antiprostatic hypertrophy agents (sitogluside), Benign prostatic hyperplasia therapy agents (e.g., tomsulosine, RBX2258), prostate growth inhibitory agents (pentomone) and radioactive agents: Fibrinogen 11 25, fludeoxyglucose F18, Flurodopa F18, Insulin 1125, lobenguane 1123, lodipamide sodium 1131, lodoantipyrine 1131, lodocholesterol 1131, Iodopyracet 1125, Iofetamine HCL 1123, Iomethin 1131, Iomethin 1131, Iothalamate sodium 1125, Iothalamate 1131, Iotyrosine 1131, Liothyronine 1125, Merosproprol Hgl 97, Methyl ioodobenzoguanine (MIB G-I131 or MIB GI 123), selenomethionine S e75, Technetium Tc99m furifosmin, technetium Tc99m gluceptate, Tc99m Biscisate, Tc99m disofenin, TC99m gluceptate, Tc99m lidofenin, Tc99m mebrofenin, Tc99m medronate and sodium salts thereof, Tc99m mertiatide, Tc99m oxidronate, Tc99m pentetate and salts thereof, Tc99m sestambi, Tc99m siboroxime, Tc99m succimer, Tc99m sulfur colloid, Tc 99m teboroxime, Tc 99m Tetrofosmin, Tc99m Tiatide, Thyroxine 1125, Thyroxine 1131, Tolpovidone 1131, Triolein 1125 and Treoline 1125, and Treoline 131, MIBG-I123 and MIBG 1131.

In some embodiments, the compounds described herein are administered in combination with one or more immune checkpoint inhibitors, kinase inhibitors, tubulin inhibitors, or topoisomerase inhibitors.

In some embodiments, the compounds described herein are administered in combination with one or more immune checkpoint inhibitors. Immune checkpoint inhibitors include any agent that blocks or inhibits in a statistically significant manner, the inhibitory pathways of the immune system. Illustrative immune checkpoint targets for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, $\gamma\delta$, and memory CD8+ ($\alpha\beta$) T cells), CD160 (also referred to as BY55), CGEN-15049, CHK 1 and CHK2 kinases, A2aR and various B-7 family ligands. B7 family ligands include, but are not limited to, B7-1, B7-2, B7-DC, B7-H1, B7-H2, B7-H3, B7-H4, B7-H5, B7-H6 and B7-H7. Immune checkpoint inhibitors include antibodies, or antigen binding fragments thereof, other binding proteins, biologic therapeutics or small molecules, that bind to and block or inhibit the activity of one or more of CTLA-4, PDL1, PDL2, PD1, BTLA, HVEM, TIM3, GAL9, LAG3, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Checkpoint protein ligands include, but are not limited to PD-L1, PD-L2, B7-H3, B7-H4, CD28, CD86 and TIM-3.

In one embodiment, the present invention covers the compounds of the present invention may be used with one or more additional therapeutics that block the interaction between immune checkpoint receptor programmed cell death protein 1 (PD-1) and its ligand PD-L1. See A. Mullard, "New checkpoint inhibitors ride the immunotherapy tsunami," Nature Reviews: Drug Discovery (2013), 12:489-492. PD-1 is expressed on and regulates the activity of T-cells. Specifically, when PD-1 is unbound to PDL-1, the T-cells can engage and kill target cells. However, when PD-1 is bound to PDL-1 it causes the T-cells to cease engaging and killing target cells. Furthermore, unlike other checkpoints, PD-1 acts proximately such the PDLs are overexpressed directly on cancer cells which leads to increased binding to the PD-1 expressing T-cells.

In another aspect, the compounds of the present disclosure may be used in combination with antibodies that can act as agonists of PD-1 and which thereby modulate immune responses regulated by PD-1. In one embodiment, the anti-PD-1 antibodies can be antigen-binding fragments. Anti-PD-1 antibodies disclosed herein are able to bind to human PD-1 and agonize the activity of PD-1, thereby inhibiting the function of immune cells expressing PD-1. In some embodiments, the compounds of the present disclosure may be used in combination with one or more PD-1 inhibitors selected from pembrolizumab, nivolumab, cemiplimab, spartalizumab, camrelizumab, sintilimab, tislelizumab, toripalimab, nivolumab, AMP-224, or AMP-514. In some embodiments, the compounds of the present disclosure may be used in combination with one or more PD-L1 inhibitors selected from atezolizumab, avelumab, durvalumab, KN035, CK-301, AUNP12, CA-170, or BMS-986189.

In some embodiments, the compounds of the present disclosure may be used in combination with one or more therapeutic agents that inhibit CTLA-4. Suitable anti-CTLA4 antagonist agents for use herein, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., Proc. Natl. Acad. Sci. USA, 95(17):10067-10071 (1998); Camacho et al., J. Clin. Oncology, 22(145): Abstract No. 2505 (2004) (antibody CP-675206); Mokyr et al., Cancer Res., 58:5301-5304 (1998), and U.S. Pat. Nos. 5,977,318, 6,682,736, 7,109,003, and 7,132,281. Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the costimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the costimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the costimulatory pathway, RNAi inhibitors (both single and double stranded) of CD28, CD80, CD86, CTLA4, among other members of the co-stimulatory pathway, among other anti-CTLA4 antagonists.

In some embodiments, the compounds of the present disclosure may be used in combination with one or more therapeutic agents that inhibit TIM-3. Blocking the activation of TIM-3 by a ligand, results in an increase in Th1 cell activation. Furthermore, TIM-3 has been identified as an important inhibitory receptor expressed by exhausted CD8+ T cells. TIM-3 has also been reported as a key regulator of nucleic acid mediated antitumor immunity. In one example, TIM-3 has been shown to be upregulated on tumor-associated dendritic cells (TADCs).

Methods of Administration

The compounds as used in the methods described herein can be administered by any suitable method and technique presently or prospectively known to those skilled in the art. For example, the active components described herein can be formulated in a physiologically- or pharmaceutically-acceptable form and administered by any suitable route known in the art including, for example, oral and parenteral routes of administering. As used herein, the term "parenteral" includes subcutaneous, intradermal, intravenous, intramuscular, intraperitoneal, and intrasternal administration, such as by injection. Administration of the active components of their compositions can be a single administration, or at continuous and distinct intervals as can be readily determined by a person skilled in the art.

Compositions, as described herein, comprising an active compound and an excipient of some sort may be useful in a variety of medical and non-medical applications. For example, pharmaceutical compositions comprising an active compound and an excipient may be useful for the treatment or prevention of an infection with a *Mycobacterium.*

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and Remington: The Science and Practice of Pharmacy, 21st Edition (Lippincott Williams & Wilkins, 2005).

Exemplary excipients include, but are not limited to, any non-toxic, inert solid, semisolid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray. In some embodiments, the active compounds disclosed herein are administered topically.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid. Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, varoius gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacrylic acid/acrylamide copolymer, polyalkylene oxides such as polyethylene oxide, polypropylene oxide, poly(ethylene oxide-propylene oxide), and a Pluronic polymer, polyoxy ethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy (Polyethylene glycol)-1000], 1,2-Distearoyl-sn-glycero-3-Phosphoethanolamine-N-[Methoxy (Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly (meth) acrylic acid, and esters amide and hydroxy alkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art. The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are put forth so as to provide those of ordinary skill in the art with a complete disclosure and description of how the compounds, compositions, and/or methods claimed herein are made and evaluated, and are intended to be purple exemplary of the disclosure and are not intended to limit the scope of what the inventors regard as their disclosure. Efforts have been made to ensure accuracy with respect to numbers but some errors and deviations should be accounted for.

Example 1. Inhibition of IL1b-Induced NF-κB Activation in ST2 Cells with Compound 1

UR241-2 having the chemical structure:

(UR241-2)

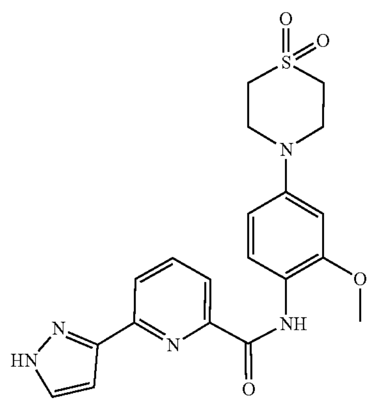

was administered to ST2 cells.

Procedure: For drug treatment, $1\times10^4$ THP-1 NF-κB-luciferase-reporter cells per well were seeded in the 96-well white plate in RPMI/0.5% FBS medium. Small molecule compounds were serially diluted in RPMI/0.5% FBS medium and pre-incubated with cells for 30 minutes at 37° C. Human IL-1(3 was added into well to the final concentration of 10 ng/mL and the plate was incubated for another 6 hours at 37° C. Luciferase assay was performed using ONE-Glo Luciferase Assay System (Promega) according to the manufacturer's protocol. Briefly, 100 μL of ONE-Glo Reagent was added per well (1:1) and waited at least 3 minutes to allow complete cell lysis. Luminescence was measured by Synergy 2 microplate reader (BioTek).

Method for synthesis: Commercially available acid was coupled with substituted anilines in anhydrous DMF using DCC. Briefly, to a solution of substituted pyridine carboxylic acid was added equimolar DCC and stirred at ice-temperature for 20 minutes. Equimolar substituted anilines were then added and reaction mixture was stirred overnight. DMF was removed under reduced pressure using Buchi rotavapor. Ice mixture was added to the reaction mixture and triturated. Separated crude solid was filtered. A small portion of the crude was purified using preparative TLC plates. The pure compound band was extracted from the prep-TLC plate. The compound was stripped off the silica gel using MeOH/DCM (90:10). The solvent was evaporated and the compound was stored at −20° C. for studies. The structure of the compounds were confirmed using high-resolution mass spectrometry (HRMS).

Representative compounds UR241-1 and UR241-2 were prepared according to the above synthetic procedure:

(UR241-1)

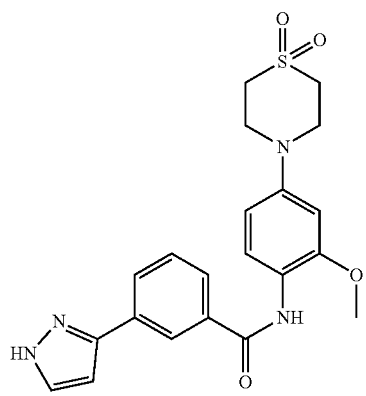

and (UR241-2)

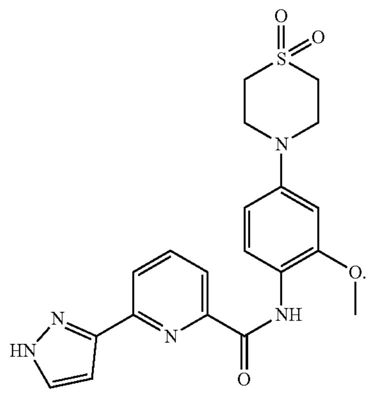

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A compound selected from:

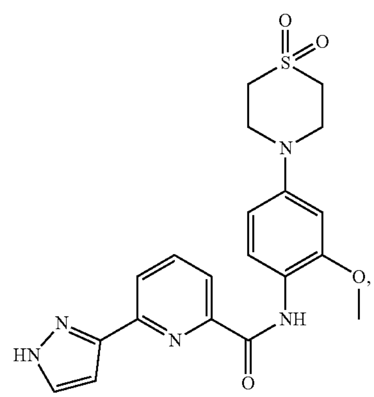

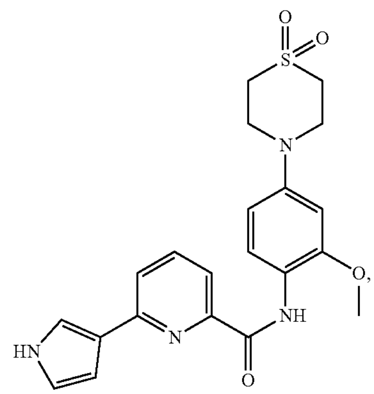

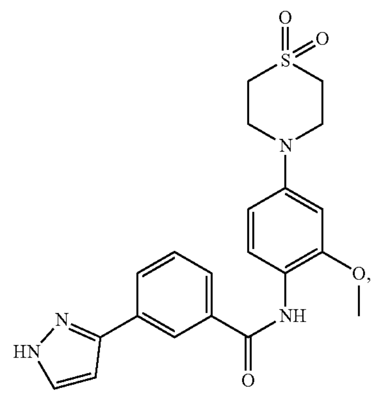

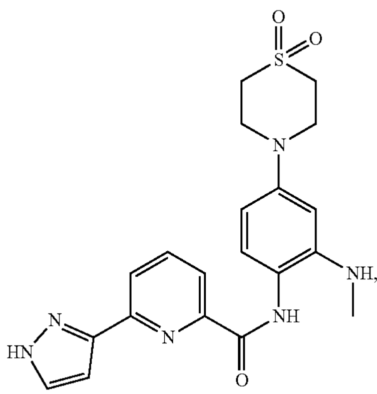

-continued
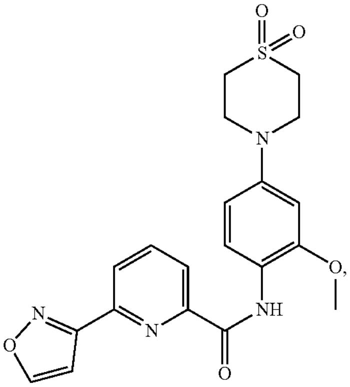
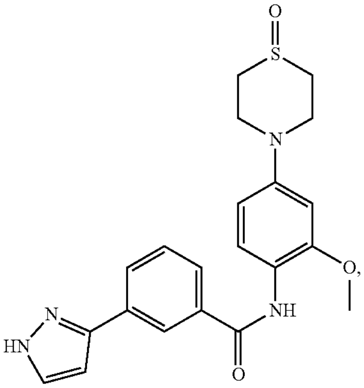
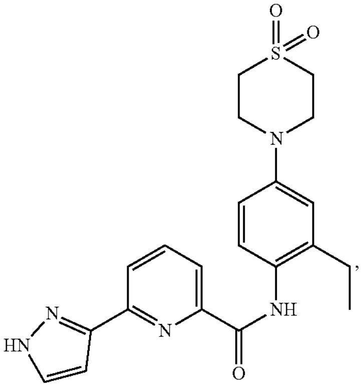
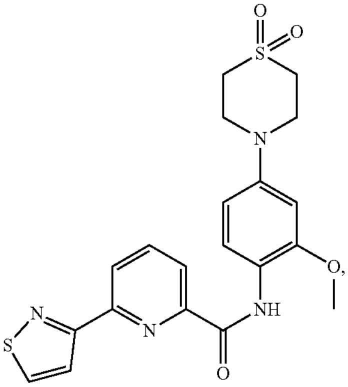
-continued
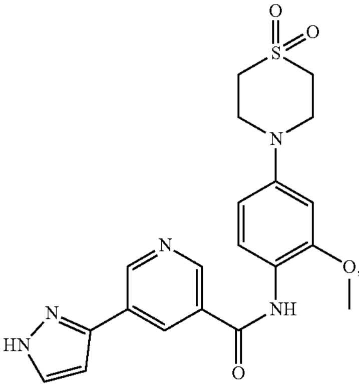
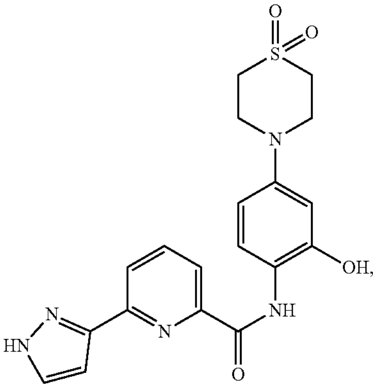
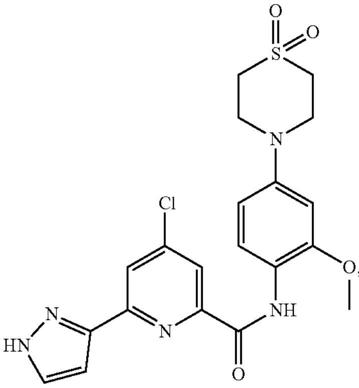
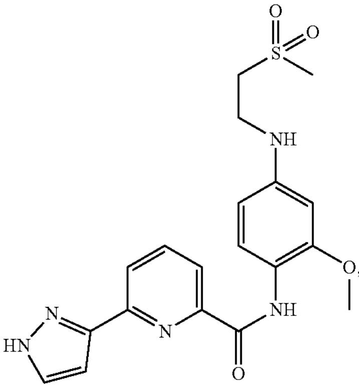

-continued

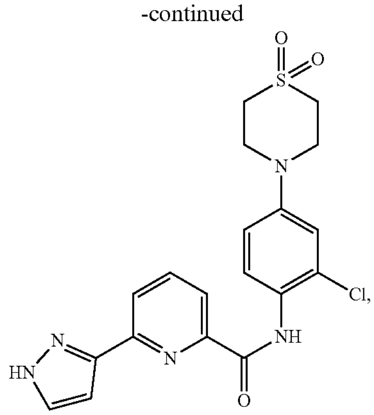

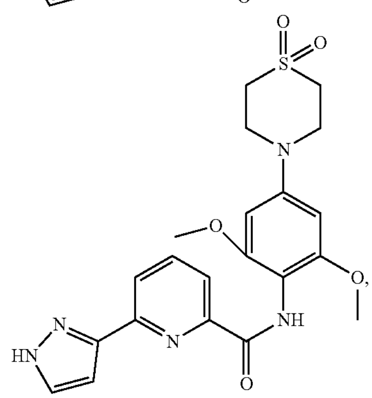

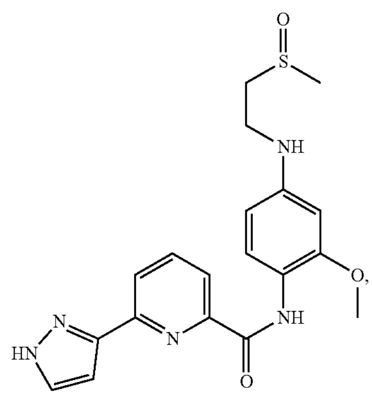

-continued

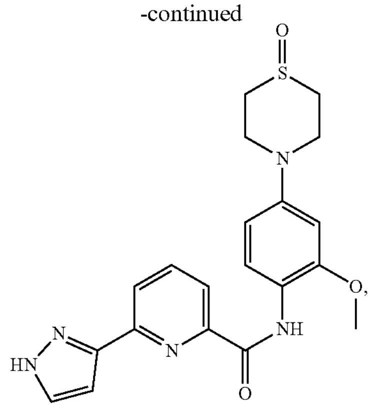

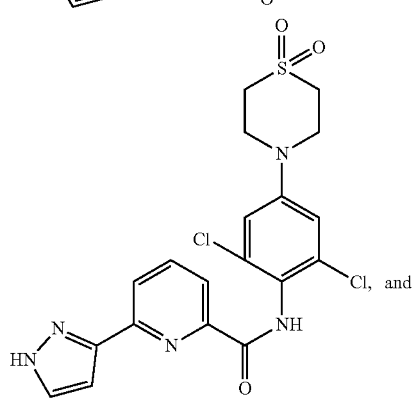

and

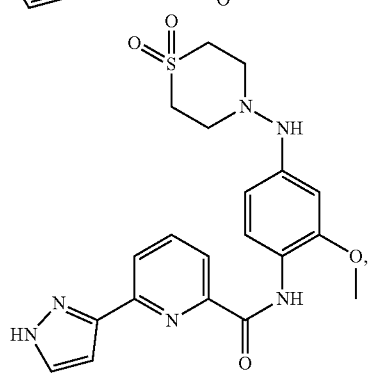

or a pharmaceutically acceptable salt thereof.

2. A pharmaceutical composition comprising a compound of claim 1, or a pharmaceutically acceptable salt thereof, and a pharmaceutically acceptable carrier.

3. A method for ameliorating pancreatic cancer, leukemia, and myeloma in a subject in need thereof comprising administering to the subject a therapeutically effective amount of a compound of claim 1, or a pharmaceutically acceptable salt thereof.

* * * * *